US012599755B2

(12) United States Patent
Salerno

(10) Patent No.: US 12,599,755 B2
(45) Date of Patent: Apr. 14, 2026

(54) VASCULAR CATHETER AND METHOD

(71) Applicant: I-VASC S.R.L., Milan (IT)

(72) Inventor: Mario Salerno, Milan (IT)

(73) Assignee: I-VASC S.R.L., Milan (IT)

( * ) Notice: Subject to any disclaimer, the term of this patent is extended or adjusted under 35 U.S.C. 154(b) by 891 days.

(21) Appl. No.: 17/426,267

(22) PCT Filed: Jan. 28, 2020

(86) PCT No.: PCT/IB2020/050647
§ 371 (c)(1),
(2) Date: Jul. 28, 2021

(87) PCT Pub. No.: WO2020/157648
PCT Pub. Date: Aug. 6, 2020

(65) Prior Publication Data
US 2022/0105319 A1      Apr. 7, 2022

(30) Foreign Application Priority Data

Jan. 28, 2019     (IT) ........................ 102019000001223

(51) Int. Cl.
A61M 25/10          (2013.01)
A61M 3/00          (2006.01)
(Continued)

(52) U.S. Cl.
CPC ........ A61M 25/1011 (2013.01); A61M 3/005 (2013.01); A61M 5/1408 (2013.01);
(Continued)

(58) Field of Classification Search
CPC ...... A61M 25/1011; A61M 2025/1013; A61M 2025/1015; A61M 25/104;
(Continued)

(56) References Cited

U.S. PATENT DOCUMENTS 4,423,725 A * 1/1984 Baran ................... A61B 17/22
                                                                              604/101.02
4,824,436 A * 4/1989 Wolinsky ........... A61M 25/104
                                                                              604/509
(Continued)

FOREIGN PATENT DOCUMENTS

WO          9831405 A2      7/1998
WO      2008068273 A2      6/2008
(Continued)

OTHER PUBLICATIONS

International Search Report and Written Opinion for corresponding PCT/IB2020/050647 mailed May 29, 2020, 15 Pages.
(Continued)

*Primary Examiner* — Michael J Tsai
*Assistant Examiner* — Forrest Blake Dipert
(74) *Attorney, Agent, or Firm* — Armstrong Teasdale LLP

(57)                    ABSTRACT

A vascular catheter includes a catheter shaft having a distal end, a proximal end, a handle, at least two occlusion elements adapted to isolate a volume of the blood vessel, and an expandable balloon, between the two occlusion elements. The catheter shaft includes a first hole that opens into the expandable balloon. The catheter handle includes a first pumping device associated with a first path and with a first tank containing a first fluid, a second pumping device associated with a second path and with a second tank containing a second fluid, and a synchronization device connectable both to the first and to the second pumping devices.

17 Claims, 12 Drawing Sheets

(51) Int. Cl.

| | |
|---|---|
| *A61M 5/14* | (2006.01) |
| *A61M 5/145* | (2006.01) |
| *A61M 25/00* | (2006.01) |
| *A61M 25/01* | (2006.01) |

(52) U.S. Cl.
CPC ...... *A61M 5/1452* (2013.01); *A61M 25/0026* (2013.01); *A61M 25/0136* (2013.01); *A61M 25/10181* (2013.11); *A61M 25/10184* (2013.11); *A61M 25/10185* (2013.11); *A61M 2025/0001* (2013.01); *A61M 25/0097* (2013.01); *A61M 2025/1015* (2013.01); *A61M 25/10182* (2013.11); *A61M 25/10188* (2013.11); *A61M 2025/105* (2013.01); *A61M 2025/1052* (2013.01); *A61M 2025/1095* (2013.01); *A61M 2205/3334* (2013.01)

(58) Field of Classification Search
CPC ...... A61M 2025/1052; A61M 25/0026; A61M 2025/105; A61M 25/10187; A61M 25/10188; A61M 25/1025; A61M 2025/1061; A61M 2205/3334; A61M 25/1018; A61M 25/10181; A61M 25/10184; A61M 2025/1068; A61B 2018/0025; A61B 2018/0022
See application file for complete search history.

(56) References Cited

U.S. PATENT DOCUMENTS

| | | | | |
|---|---|---|---|---|
| 5,328,471 | A * | 7/1994 | Slepian | A61L 24/0031 604/101.03 |
| 5,439,446 | A * | 8/1995 | Barry | A61M 25/104 604/103.01 |
| 6,494,861 | B1 * | 12/2002 | Tsukernik | A61M 25/10184 604/67 |
| 7,184,827 | B1 * | 2/2007 | Edwards | A61M 25/1011 604/509 |
| 2003/0065303 | A1 * | 4/2003 | Wellman | A61M 25/1011 604/500 |

| | | | | |
|---|---|---|---|---|
| 2004/0243057 | A1 * | 12/2004 | Vinten-Johansen .. | A61M 25/10 604/97.01 |
| 2005/0209674 | A1 * | 9/2005 | Kutscher | A61M 25/1011 623/1.11 |
| 2006/0271151 | A1 * | 11/2006 | McGarry | A61M 25/1011 623/1.11 |
| 2006/0276743 | A1 * | 12/2006 | MacMahon | A61M 1/81 604/28 |
| 2009/0281483 | A1 | 11/2009 | Baker et al. | |
| 2011/0218494 | A1 * | 9/2011 | Gerrans | A61B 17/320725 604/101.05 |
| 2012/0226230 | A1 * | 9/2012 | Gerrans | A61B 5/4839 604/103.01 |
| 2012/0277525 | A1 * | 11/2012 | O'Dea | A61B 5/0538 604/8 |
| 2016/0074581 | A1 * | 3/2016 | Gerrans | A61B 5/0215 600/301 |
| 2016/0213894 | A1 * | 7/2016 | Salerno | A61M 25/1002 |
| 2016/0263319 | A1 * | 9/2016 | Brandeis | A61M 1/815 |
| 2016/0302822 | A1 | 10/2016 | Tal et al. | |
| 2016/0339213 | A1 * | 11/2016 | Martin | A61K 31/45 |
| 2017/0259043 | A1 * | 9/2017 | Chan | A61M 29/02 |
| 2019/0143038 | A1 * | 5/2019 | Anand | A61M 25/0045 600/432 |
| 2020/0078602 | A1 * | 3/2020 | Hirsh | A61N 5/103 |
| 2020/0101269 | A1 * | 4/2020 | Hayes | A61B 17/12136 |
| 2020/0147295 | A1 * | 5/2020 | Van Niekerk ... | A61M 25/10181 |
| 2021/0236140 | A1 * | 8/2021 | Epshtein | A61B 17/22 |
| 2023/0248949 | A1 * | 8/2023 | Narisawa | A61M 1/772 604/28 |
| 2024/0050714 | A1 * | 2/2024 | Mitra | A61M 25/007 |

FOREIGN PATENT DOCUMENTS

| | | | | |
|---|---|---|---|---|
| WO | WO-2010062778 A2 * | 6/2010 | | A61B 1/04 |
| WO | WO-2019089392 A1 * | 5/2019 | | A61B 1/00082 |

OTHER PUBLICATIONS

IPRP for corresponding PCT/IB2020/050647 mailed Jan. 19, 2021, 23 Pages.

* cited by examiner

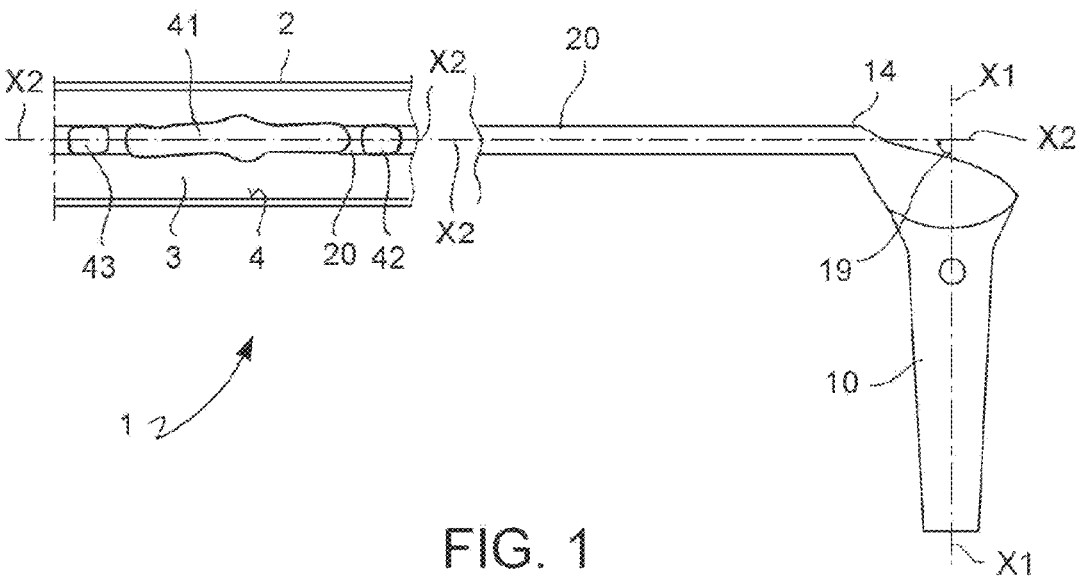
FIG. 1
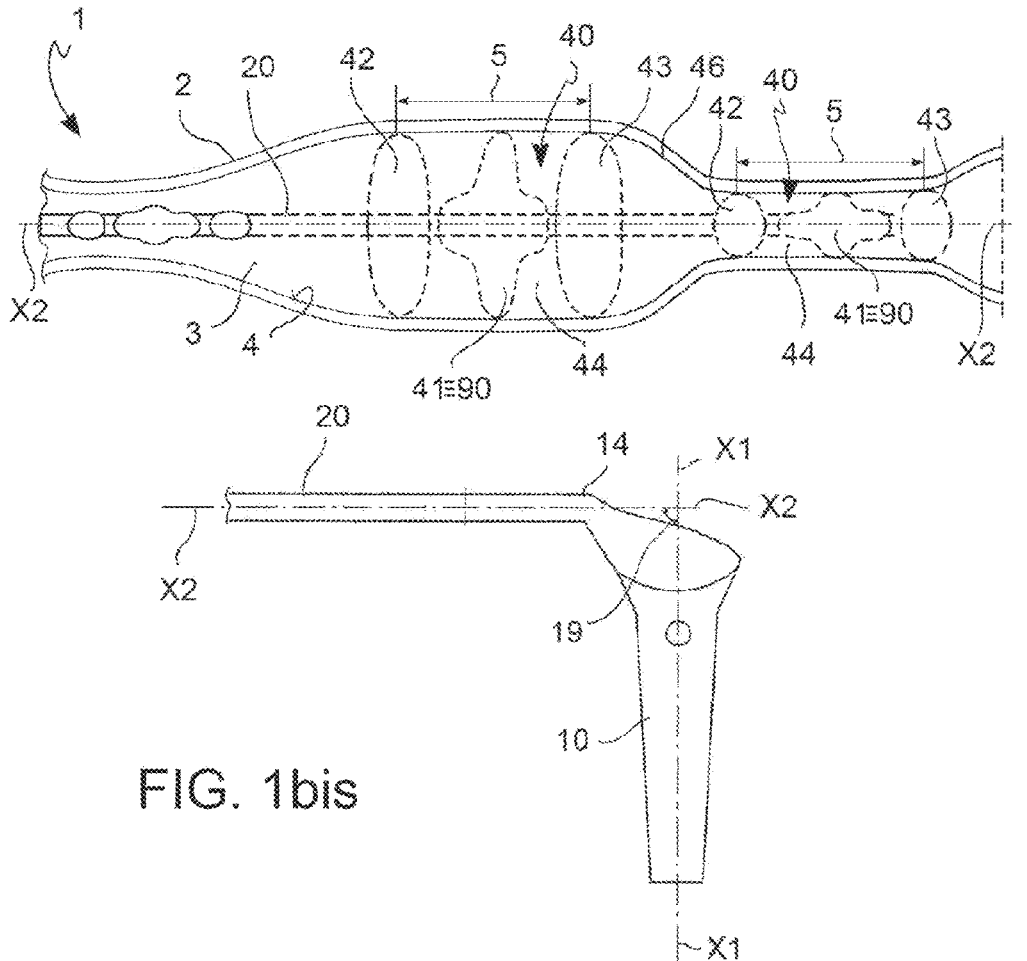
FIG. 1bis

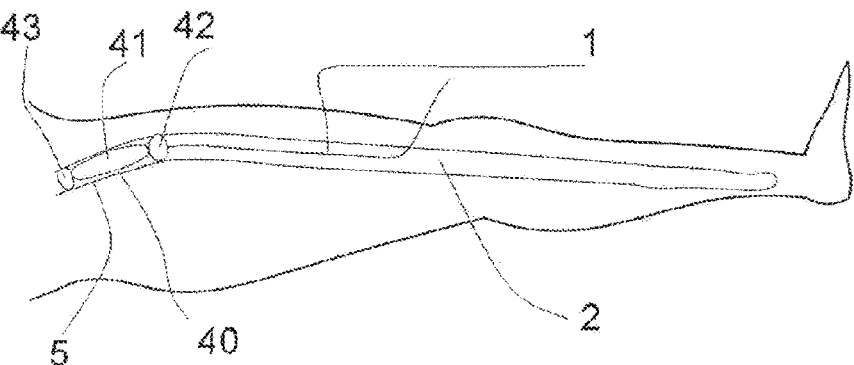
FIG. 23
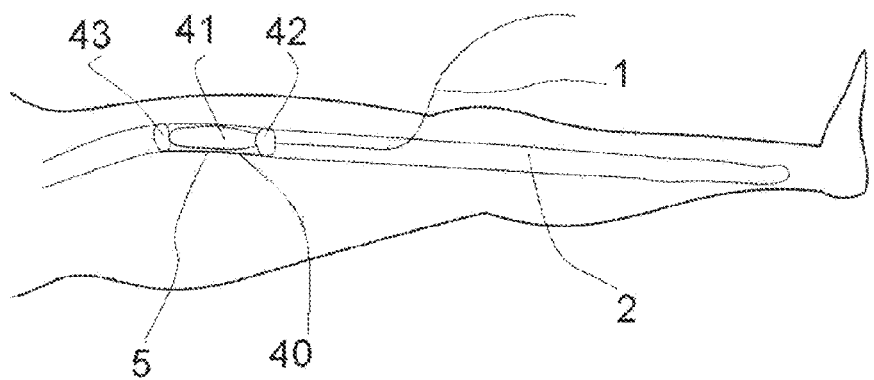
FIG. 23bis
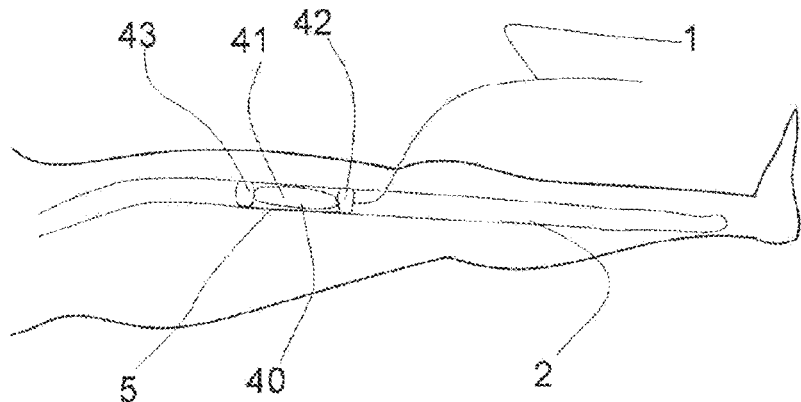
FIG. 23ter

VASCULAR CATHETER AND METHOD

CROSS-REFERENCE TO RELATED APPLICATIONS

This application is a National Phase Application of PCT International Application No. PCT/IB2020/050647, having an International Filing Date of Jan. 28, 2020, which claims priority to Italian Application No. 102019000001223, filed Jan. 28, 2019, each of which is hereby incorporated by reference in its entirety.

FIELD OF THE INVENTION

The present invention relates to a vascular catheter.

The vascular catheter according to the invention is particularly suitable for carrying out a targeted local pharmacological treatment.

The present invention relates to a method.

BACKGROUND ART

In clinical practice it is generally known to introduce a catheter shaft inside a lumen of the human body.

In the case of the treatment of arteries (angioplasty), a stent is typically implanted by vascular catheter in the artery area with a reduced section due to the accumulation of lipid plaques in order to restore the original diameter of the artery by mechanical action exercised by the stent expanded by an expandable balloon fitted onto the catheter shaft. It is also known to crush the material occluding the vein in vivo, particularly when rich in calcium, to eliminate arterial occlusion by using a device adapted to treat the plaque with pulsating ultrasonic excitation.

An undesirable complication of the application of these known therapies appears with the formation of thrombi caused for example by the detachment of tissue fragments from the vessel wall or from the body of the treated plaque. The thrombi being insoluble in the blood can migrate into the patient's vascular system and in some unfavorable conditions they can occlude a blood vessel (artery or vein) necessarily blocking the flow of blood to or from a specific anatomical district.

For example, document US-2006-0276743 describes a catheter for washing a blood vessel from debris, which shows in particular the removal of insoluble solid fragments from a patient's vascular system, obtained through the creation by catheter of a blood stream inside the artery in the proximity of the treated region. The catheter therefore has an irrigation hole and a suction hole in its distal portion facing the same volume of fluid, and the blood stream is generated between the irrigation hole and the suction hole of the catheter. Such a blood stream thus generated conveys the suspended embolic fragments inside the suction hole. The catheter further comprises a handle at the proximal end, in which there are two syringes: one for collection downstream of the suction hole, and one for irrigation upstream of the irrigation hole. Therefore, a path is formed which connects in series the irrigation syringe, the respective catheter path which flows from the irrigation hole, the treated artery portion, the suction hole and the respective return path to the collection syringe. The catheter handle is disclosed as comprising a volumetric exchange device which couples the plungers of the irrigation syringe and the collection syringe so that they move together, one in supply and the other in suction, to generate the circuit which determines the blood stream formation.

Such a solution is not without drawbacks, since it requires irrigation in the artery to be treated of a volume of fluid which will replace a certain volume of blood during the process of suction and collection of the embolic fragments. Furthermore, such a solution necessarily requires the collection of a certain amount of blood together with the embolic fragments. Another drawback consists in the impossibility of reversing the direction of the path inside the catheter paths, in other words the supply path cannot act as a suction path even for part of the process, because it would involve the dispersion of the suspended embolic fragments in the treated artery portion. In addition, such a system requires a catheter path specifically dedicated to irrigating a fluid into the patient's vascular system and a second separate catheter path specifically dedicated to taking another fluid from the patient's vascular system, requiring a certain radial size of the vascular catheter shaft for delivery and return.

Furthermore, sclerosing treatment techniques of a blood vessel are generally known, such as for example a varicose vein, in order to mitigate in a patient the symptomatology of venous insufficiency, which typically occurs with the dilatation and tortuous course of the superficial veins as well as with the insufficiency of the venous valves which impose blood reflux phenomena otherwise destined to reach the heart pump.

For example, international patent application No. 2008-068273, in the name of the same Applicant, discloses a device adapted to assist locally the sclerosing treatment of at least a stretch of the blood vessel. Such a device comprises an intra-vascular catheter with at least two ways and provided with at least two balloons fitted thereon, adapted when in an expanded configuration to temporarily occlude a portion of a blood vessel, substantially isolating it from the blood circulation path. Therefore, one path of the catheter is dedicated to the transport of the first fluid from a tank, for example a syringe of a syringe pump, inside the balloon installed in the blood vessel. The other catheter path, however, is connected to a second tank which contains a pharmacological agent stored in the form of a liquid solution or foam. When the balloons are in an expanded configuration to isolate a stretch of blood vessel, the pharmacological agent is dispensed through the catheter into the interstices between the outer surfaces of the balloons when in the expanded configuration and the inner face of the walls of the blood vessel. In particular, one of the at least two balloon is adapted to function substantially as a core within the lumen of the blood vessel in such a way as to force the drug to position itself in the radially outer areas, i.e. which lap the wall, of the stretch of blood vessel to be treated.

Such a solution is satisfactory from many points of view in that it allows the pharmacological agent to be applied selectively to the blood vessel wall in optimal conditions, i.e. when the blood vessel has been emptied of blood, and at the same time limiting to a minimum the amount of pharmacological agent to be used due to the reduced volume of such interstices defined by the balloons, and in particular by the balloon which acts as a core, when in the expanded condition, thereby minimizing the ratio between the volume of pharmacological agent supplied and the surface of the blood vessel to be treated. Not only that, due to the balloons which act as caps placed on the longitudinally opposite sides to the balloon acting as a core, it is possible to maintain a predeterminable concentration of the pharmacological agent in contact with the vessel walls locally uniform and stable over time.

Furthermore, such a solution uses a strategy of inflation of the at least two balloons based on the sequential expansion in the radial direction of longitudinally adjacent portions of the at least two balloons, for example from the center towards their respective longitudinal ends, so as to push the blood longitudinally outside the volume occupied by the balloon during the inflation or expansion step, avoiding the undesired formation of blood pockets trapped between the outer surface of the at least two balloons and the inner wall of the segment of blood vessel to be treated.

Such a known solution, however, is not without drawbacks.

In fact, it is extremely laborious for an operator, typically a vascular surgeon, to proceed with the controlled delivery of the pharmacological agent in the interstices formed between the at least two balloons and the internal vessel wall. In fact, such a maneuver can cause an uncontrolled radial expansion of the walls of the blood vessel, risking to tear it as well as causing the migration of the drug to other collateral vessels which originate from the interstices.

The wall of the blood vessel typically consists of a series of concentric layers, the innermost of which lapped by the blood stream consists of endothelial cells. More externally inside the vessel wall there is a layer of muscle cells, or muscular tunic. Even more externally there is an additional layer, called the adventitious tunic, outside the muscular tunic, which forms the last outer layer of the vein wall.

Further different examples of systems are also known which aim to assist the sclerosing treatment of varicose veins, as shown for example by document US-2016-0302822 which discloses a vascular catheter provided with an outflow end of the pharmacological agent inclined and radially eccentric relative with respect to the longitudinal axis of the catheter so as to come into contact with a portion of the vein wall when the catheter is installed in the blood vessel. This solution uses a catheter rotatable around its longitudinal axis moved by a motorized device housed in the catheter handle. The catheter handle is in turn provided with a trigger for operating such a rotary electric motor.

This solution, although partially advantageous in not requiring the provision of balloons fitted onto the catheter, and therefore by the ability to empty and isolate a portion of the blood vessel, is by no means without drawbacks. First of all, the risk of uncontrolled laceration of the vessel and in particular of its collateral vessels due to the involuntary twisting of the vessel itself caused by the rotating end of the catheter is very frequent, especially where the anatomy to be treated has tortuosity or bifurcations, for example due to the presence of collateral branches of the blood vessel, which in fact limits the use thereof to substantially rectilinear vein stretches or characterized by a gentle curvature and lack of large collateral vessels. Furthermore, with the use of such a catheter, the time of application of the drug to the wall of the blood vessel to be treated is reduced to a minimum, resulting in the need to increase the dosage of the pharmacological agent for the same sclerosing effect obtained. In other words, the delivery strategy of the pharmacological agent described in such a document is not very controllable since the drug, even though delivered towards the vessel wall, is subject to the blood flow, modulated by the breathing cycle, the heart rate, the position of the limb during treatment and the caliber, a flow which tends to transport it both through stretches characterized by high vorticity and therefore by random motion, and through stretches in which the blood flow is substantially laminar and therefore the transport occurs substantially along the median axis of the vessel itself, removing the agent from the vein wall. Therefore, these types of solutions are unsuitable for keeping under control the time of application of the pharmacological agent as well as the concentration of pharmacological agent.

The need is therefore strongly felt to provide a solution capable of delivering in a controlled manner a pharmacological agent in a segment of a blood vessel to be treated, for example a varicose vein, by means of a catheter which at the same time allows minimizing the ratio between the volume of pharmacological agent delivered and the surface of the walls of the lumen to be treated.

The need is also felt to reduce the risk of human errors in the maneuverability of a catheter with at least two ways.

Solution

It is an object of the present invention to overcome the drawbacks mentioned with reference to the prior art and to suggest a solution to the above needs.

This and other objects are achieved by a vascular catheter according to claim 1.

Some advantageous embodiments are the subject of the dependent claims.

According to an aspect of the catheters and methods according to the invention, a vascular catheter comprises a catheter shaft, and a catheter handle at the proximal end of the catheter shaft, and at least two occlusion elements, for example two expandable occlusion balloons, adapted to act as an occluder to isolate an isolated volume of the blood vessel longitudinally interposed between said at least two occlusion elements, and an expandable balloon longitudinally interposed between the two occlusion elements and adapted to act as a core to occupy a first portion of the isolated volume of the blood vessel.

According to an aspect of the catheters and methods according to the invention, the vascular catheter comprises at least two delivery and return catheter paths, and the catheter shaft comprises a first hole which leads into the at least one expandable balloon adapted to act as a core, the first hole is in fluid communication with the first path, the catheter handle comprises a first pumping device associable with a first tank containing a first fluid, for example physiological solution; and wherein the catheter shaft comprises a second hole which opens out from the at least one expandable balloon so as to be adapted to lead into a second portion of said isolated volume, the second hole is in fluid communication with the second path, the catheter handle comprises a second pumping device associable with a second tank containing a second fluid, for example a drug.

According to an aspect of the catheters and methods according to the invention, a synchronization device may be operatively connected both to the first pumping device and to the second pumping device so that when said synchronization device (60) is operatively connected to both said first pumping device and said second pumping device, the catheter handle can deliver in said isolated volume a predetermined volume of second fluid out of the at least one expandable balloon simultaneously causing a reduction in volume of the expandable balloon by an equal predetermined volume.

According to an aspect of the catheters and of the methods according to the invention, the synchronization device when operatively connected to both said first pumping device and said second pumping device is adapted to take from said isolated volume a predetermined volume of second fluid simultaneously causing an expansion of volume of the expandable balloon by an equal predetermined volume.

According to an aspect of the catheters and methods according to the invention, the volume reduction of the expandable balloon is determined by suction of said first fluid from the expandable balloon.

According to an aspect of the catheters and methods according to the invention, by supplying said first fluid into the expandable balloon a volume expansion of the expandable balloon is determined.

According to an aspect of the catheters and of the methods according to the invention, the catheter shaft may be repositioned so as to adapt itself to portions of blood vessels of various dimensions, thus creating an isolated volume on various different portions of the vessel to be treated.

DRAWINGS

Further features and advantages of the catheter according to the invention will become readily apparent from the following description of preferred exemplary embodiment thereof, provided merely by way of a non-limiting example, with reference to the accompanying drawings, in which:

FIG. 1 shows a schematic view of a vascular catheter, according to an embodiment;

FIG. 1b is shows a schematic view of a vascular catheter, according to an embodiment;

FIGS. 23, 23b is and 23ter diagrammatically show the repositioning of the vascular catheter, according to an embodiment;

Figure 24:
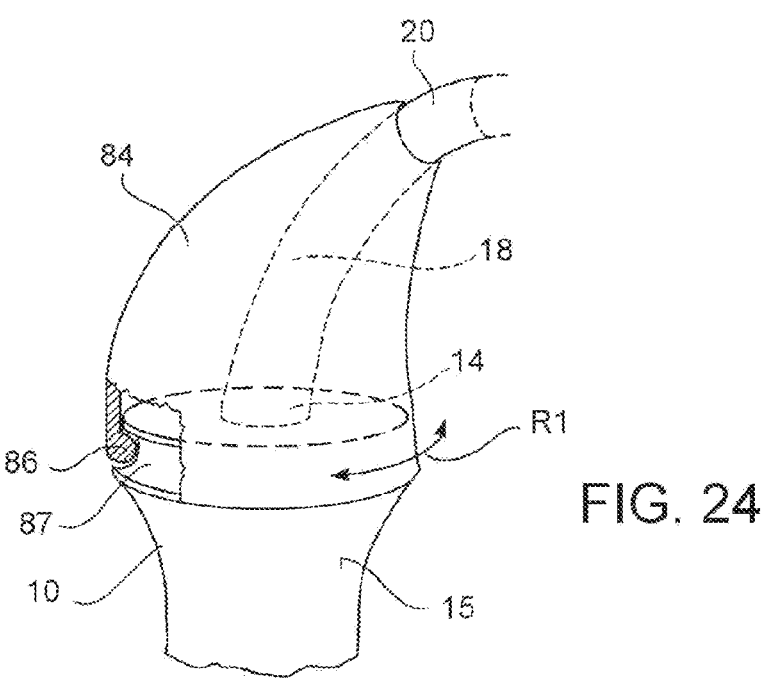
Figure 25:
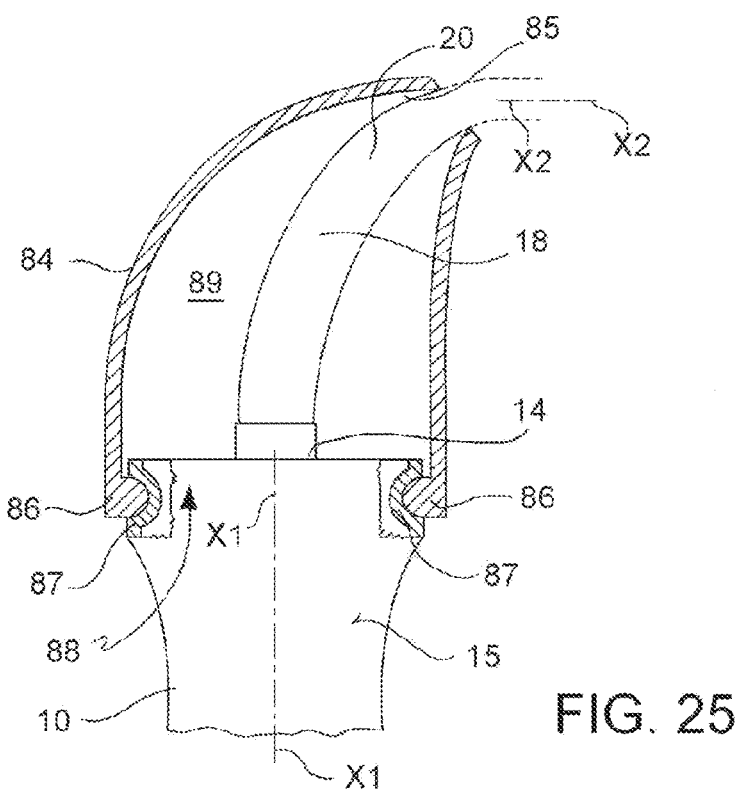

FIGS. 24 and 25 diagrammatically show a portion of a catheter, according to an embodiment.

DETAILED DESCRIPTION OF SOME
PREFERRED EMBODIMENTS

According to a general embodiment, a vascular catheter 1 is provided.

The vascular catheter 1 is particularly adapted to carry out a targeted drug therapy in at least a localizable portion of a patient's vascular system.

The vascular catheter 1 comprises a catheter shaft 20 having a distal end, a proximal end 14 and a longitudinal axis X2 therebetween.

The catheter shaft 20 is adapted to reach at least a predefined position in a blood vessel 2 in a patient.

The vascular catheter 1 comprises a catheter handle 10 placed at the proximal end 14 of the catheter shaft 20.

The vascular catheter 1 comprises at least two occlusion elements 42, 43 or cap elements 42, 43, fitted onto the catheter shaft 20 adapted to act as an occluder, or as a cap, to isolate from the blood circulation an isolated volume 40 of the blood vessel 2 longitudinally interposed between said at least two occlusion elements 42, 43. Preferably, said at least two occlusion elements 42, 43 are designed to longitudinally isolate an isolated volume 40 inside the blood vessel 2, defining a vessel segment 5 to be treated therebetween.

For example, for the sclerosing treatment of varicose veins, the occlusion elements 42, 43 will be arranged one proximally and one distally with respect to the vein region 5 to be treated with a sclerosing drug. The provision of said occlusion elements 42, 43 allows preventing the physiological blood supply in the vessel segment to be treated.

The vascular catheter 1 comprises an expandable balloon 41, longitudinally interposed between the two occlusion elements 42, 43 and adapted to act as a core to occupy a first portion 90 of the isolated volume 40 of the segment 5 to be treated of the blood vessel 2. Preferably, said first portion 90 of the isolated volume 40 corresponds to the volume of the expandable balloon 41 which acts as a core.

The vascular catheter 1 comprises at least two delivery and return handle paths 11, 12, 13, independent from each other, which mutually define in the vascular catheter 1 at least a first path P1 and at least a second path P2, distinct from the first path P1. In this way, the at least two handle paths can be at least two separate and distinct paths.

The catheter shaft 20 comprises a first hole 24 or first opening 24 which opens into the at least one expandable balloon 41 adapted to act as a core. Through the first hole 24 it will be possible, if necessary, to inflate the expandable balloon 41, thereby expanding it.

Advantageously, the first hole 24 is in fluid communication with said first path P1 and the catheter handle 10 comprises a first pumping device 31 associated with the first path P1 and associable with a first tank 32 containing a first fluid 30. The first pumping device 31 is adapted to move the first fluid 30 from the first tank 32 towards the expandable balloon 41 as well as from the expandable balloon 41 to the first tank 32.

With further advantage, the catheter shaft 20 comprises a second hole 26 which opens out of the at least one expandable balloon 41 so as to be adapted to lead into a second portion 44 of said isolated volume 40. Preferably the second portion 44 of the isolated volume 40 is an interstitial volume delimited by the wall 45 of the expandable balloon 41 which acts as a core, by at least one of the occlusion elements 42, 43, and by the vessel wall 4 of the segment 5 to be treated of the blood vessel 2.

The second hole 26 is in fluid communication with said second path P2, and the catheter handle 10 comprises a second pumping device 51 associated with the second path P2 and associable with a second tank 52 containing a second fluid 50, for example pharmacological fluid 50. The second pumping device 51 is adapted to move the second fluid 50 from the second tank 52 towards the second portion 44 of the isolated volume 40 as well as from the second portion 44 of the isolated volume 40 to the second tank 32.

The catheter handle 20 further comprises a synchronization device 60 operatively connectable both to the first pumping device 31 and to the second pumping device 51.

In this way, when said synchronization device 60 is operatively connected to both said first pumping device 31 and said second pumping device 51, the catheter handle 10 can deliver in said isolated volume 40 a predetermined volume of second fluid 50 out of the at least one expandable balloon 41.

At the same time, a reduction in the volume of the expandable balloon 41 by an equal predetermined volume is determined.

According to a preferred embodiment, the volume reduction of the expandable balloon 41 is determined by suction of said first fluid 30 from the expandable balloon 41. Preferably, the suction of said first fluid 30 is carried out by the catheter handle 10, so as to bring a predetermined volume of first fluid 30 out of the expandable balloon 41, collecting it at least in part in the first tank 30. The at least one catheter path 11, 12, 13 dedicated to said first fluid 30 therefore acts as a delivery and return path.

According to a variant, the volume reduction of the expandable balloon 41 is determined by the contraction of said first fluid 30 inside the expandable balloon 41. For example, said first fluid 30 may contain gas adapted to undergo a volume reduction with increasing pressure in said isolated volume 40. In this way, by delivering said second fluid 50, for example pharmacological fluid, in the second portion 44 of the isolated volume 40 of the blood vessel 2, a pressure increase is determined which is transmitted by the wall 45 of the expandable balloon 41 to the first fluid 30 containing gas, which contracts. In this way, a forced delivery of a second fluid 50, for example a drug, is carried out. For example, the first fluid 30 comprises a mixture of liquid and gas. For example, the first fluid 30 is gaseous and comprises for example helium or carbon dioxide ($CO_2$).

According to an embodiment, said synchronization device 60 when operatively connected to both said first pumping device 31 and said second pumping device 51 is adapted to take from said isolated volume 40 a predetermined volume of second fluid 50 simultaneously causing an expansion of volume of the expandable balloon 41 by an equal predetermined volume.

According to an embodiment, by supplying said first fluid 30 into the expandable balloon 41 a volume expansion of the expandable balloon 41 is determined.

Due to such a vascular catheter 1, the pressure inside the isolated volume 40 of the blood vessel 2 is kept substantially unchanged and therefore the isolated volume 40 is kept substantially unchanged.

Preferably, by "isolated volume 40" it is meant a volume isolated from the blood circulation, delimited longitudinally by the occlusion elements 42, 43, even if a minimum mass exchange may occur from or to the isolated volume 40, for example collateral vessels 8 of small diameter may be present, which branch out from the second portion 44 of the isolated volume 40, in other words from the interstitial volume 44 of the isolated volume 40. Preferably, the isolated volume 40 is also defined where physiological perturbations due to the patient's respiratory reflex, the patient's heart rate variation, the patient's position occur.

Due to such a vascular catheter 1, the tanks 32, 52 are allowed to act both as a collection tank and as a storage tank.

Due to such a vascular catheter 1, the paths P1 and P2 can, if necessary, be crossed by the respective fluid 30 or 50 in both directions.

Due to such an expandable balloon 41 it is possible to distribute the pharmacological fluid towards the vessel wall 4, which is the tissue to be treated for example in the sclerosing treatment of varicose veins. In this way, improved control of pharmacological treatment is achieved.

The synchronization of the volumes which can be activated on command takes place inside the isolated volume 40 and preferably also in the handle 10 of the vascular catheter 1.

Preferably, the body of said catheter handle 10 comprises a handle casing 15 or casing 15 which forms a handle 17 adapted to be gripped in a hand of an operator, typically a surgeon.

The catheter handle 10 comprises a connection interface to the proximal end 14 of the catheter shaft 20 having at least two handle paths and adapted to form a fluid connection between said at least two handle paths and respective at least two shaft paths of the catheter shaft 20 forming at least two handle paths 11, 12, 13. Preferably, each handle path 11, 12, 13 defines an independent conduit, i.e. not in fluid communication with the conduits consisting of the other paths. At least one further path adapted to slidingly receive at least a portion of a guide wire may be provided.

Preferably, said first fluid 30 is an inflation fluid for inflating and deflating at least one expandable balloon 41.

Preferably, the term "expandable balloon" means a deformable chamber fitted onto the catheter shaft at an opening of said catheter shaft in fluid communication with a respective handle path of the catheter handle and with a pumping device for the inflation and/or deflation thereof. Preferably, the term "expandable balloon" means a chamber deformable in at least one expanded configuration, for example when inflated by inflation fluid, and at least one contracted or collapsed configuration. Preferably, during the inflation and/or deflation of the balloon, the balloon wall exerts pressure on the inflation fluid, for example said first fluid 30.

When under operating conditions, said isolated volume 40 of the segment of the vessel 5 to be treated of the blood vessel 2 comprises at least one expandable balloon 41 which acts as a core and at least a second portion 44 of isolated volume 40 or interstitial volume 44 outside the expandable balloon 41 and which laps the vessel wall 4.

Preferably, said first fluid 30 is a physiological solution, preferably in liquid form. For example, said first fluid 30 is an inflation gas.

According to a preferred embodiment, said first pumping device 31 is adapted to take said first fluid 30 from said catheter shaft 20. In this way, said first pumping device 31 is adapted to modify and in particular to deflate, by contracting it at least radially, the first portion 90 of the isolated volume 40, i.e. the portion occupied by the expandable balloon 41 which acts as a core. Preferably, said first pumping device 31 is also adapted to dispense said first fluid 30 into said catheter shaft 20, through said connection interface 14. In this way, said first pumping device 31 is adapted to inflate, radially expanding it, the first portion 90 of the isolated volume 40, i.e. the portion occupied by the expandable balloon 41 which acts as a core.

Preferably, the second fluid 50 is a solution containing a pharmacological agent preferably suitable for the sclerosing treatment of varicose veins. For example, said second fluid 50 is a solution containing: cortisone and/or antiplatelet agents, anti-inflammatory, chemotherapy, anesthetics agents, cryogenic gases, hypertonic solutions.

According to a preferred embodiment, said second pumping device 51 is adapted to deliver pharmacological fluid 50 towards said catheter shaft 20. In this way, said second pumping device 51 is adapted to administer said pharmacological fluid 50 in said second portion 44 of the isolated volume 40. According to an embodiment, said second pumping device 51 is also adapted to take the second fluid 50 from said catheter shaft 20.

In this way, i.e. when said synchronization device 60 is operatively connected to both said first pumping device 31 and said second pumping device 51, said catheter handle 10 delivers a predetermined volume of pharmacological fluid 50 and simultaneously takes an equal predetermined volume of first fluid 30.

When under operating conditions, the catheter shaft 20 is inserted into the lumen 3 of said blood vessel 2, for example a varicose vein, and said at least one expandable balloon 41 is fitted onto said catheter shaft 20 at a first shaft opening 24.

According to an embodiment, said at least two occlusion elements 42, 43 consist of two further expandable balloons or occlusion balloons 42, 43, which act as occluders when in the expanded configuration to occlude a cross section of a blood vessel 2. In this way, the vascular catheter 1 comprises at least two expandable balloons, one of which acts as a core and at least one acts as an occluder. Preferably, there are three expandable balloons, one of which acts as a core and two as an occluder. Preferably, each occlusion balloon 42, 43 is fitted onto said catheter shaft 20 and is in fluid connection with a respective third hole 25 of the catheter shaft 20, so that the first pumping device 31 is adapted to inflate it with said first fluid 30, as shown for example in FIG. 10. Preferably, said at least one occlusion balloon 42, 43 is inflated by expanding radially until it presses against the walls 4 of the blood vessel 2, occluding a cross section of the blood vessel 2 itself. By using two occlusion balloons 42, 43 longitudinally spaced apart, it is possible to isolate a volume 40 from the physiological blood flow.

In this way, the occlusion elements 42, 43 are made expandable and collapsible if necessary.

Preferably, the catheter shaft 10 can be repositioned so as to adapt itself to blood vessel portions of various size creating an isolated volume 40.

When the catheter shaft 20 is inserted into a blood vessel 2, it can be positioned in a segment 5 to be treated, and at the end of the treatment it is possible to at least partially collapse the occlusion elements 42, 43, advance or retract the catheter shaft 20, re-expand the occlusion elements 42, 43 and repeat the treatment.

For example, when the occlusion elements 42, 43 consist of expandable balloons, an operator is allowed to collapse them and expand them if necessary, to advance or retract the catheter shaft 20 into the blood vessel 2. When the catheter shaft 20 is positioned or re-positioned in a vessel portion which requires targeted localized treatment, the volume of the vessel segment to be treated is emptied by inflating the expandable balloon 41 which acts as a core, the occlusion elements 42, 43 are expanded so as to obtain said isolated volume 40. At this point, an operator can make continuous adjustments of the first and second portions 90, 44 of the isolated volume 40 by acting on the catheter handle 10 which synchronizes the expansion of a portion 90, for example by inflating the core expandable balloon 41, with the contraction of the other portion 44. This adjustment clearance can be repeated if necessary along the longitudinal extension of a blood vessel. When the occlusion elements 42, 43 are expandable balloons they can share a catheter path with the core expandable balloon 41, since they can be expanded with the same first fluid 30.

For example, the at least one third hole 25 which flows into the occlusion balloons 42, 43 is in fluid communication with said first tank 32 directly or indirectly through the interposition of a selector device 80.

When under operating conditions, the sequential inflation of said core expandable balloon 41 and of at least one occlusion balloon 42 or 43 allows completely emptying of blood a blood vessel segment 5 to be treated or vessel segment 5 to be treated or vessel stretch 5 to be treated.

Figure 6:
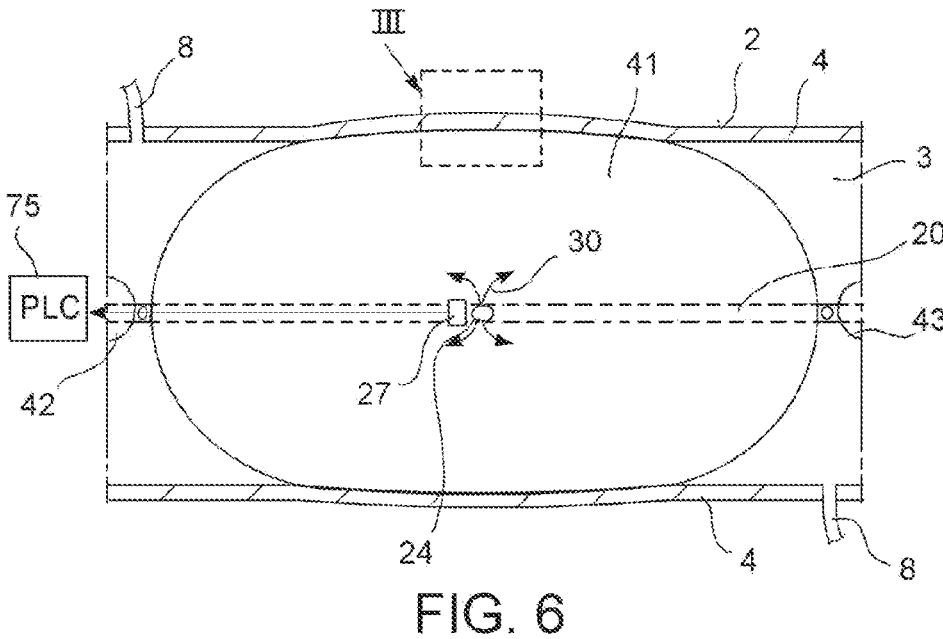
FIG. 6 is a schematic longitudinal sectional view of a portion of a catheter shaft inside a blood vessel, according to an embodiment, during the expansion by over-inflation of an expandable balloon, wherein a control device associated with said catheter handle is also diagrammatically depicted.
Figure 7:
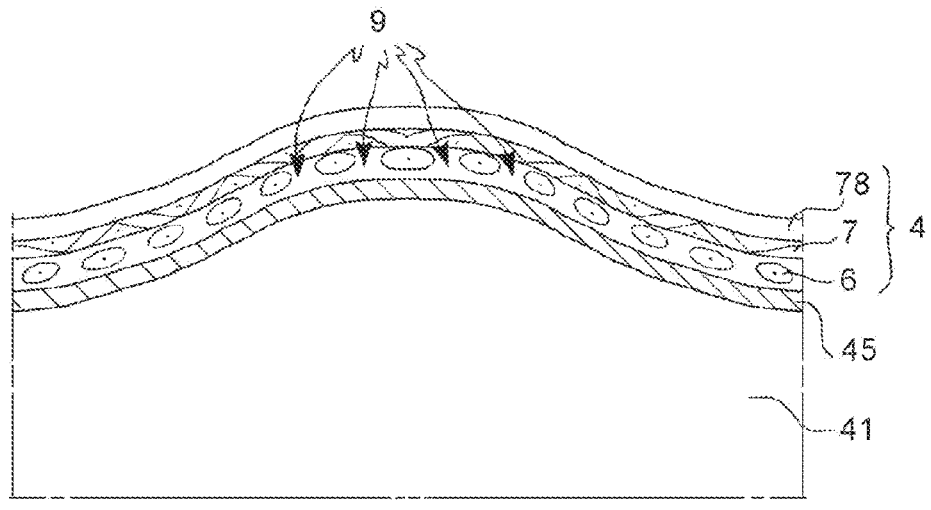
FIG. 7 is a schematic longitudinal sectional view of the portion of the blood vessel wall indicated by the arrow VII in FIG. 6.

As shown for example in FIG. 6, due to the inflation of said core balloon 41, a portion of said blood vessel 2 can be emptied of blood. The conformation and the localized stiffness properties of the core balloon 41 may be selected so that it expands radially first in a substantially spherical portion thereof adapted to contact the walls 4 of the blood vessel 2, and subsequently expands in at least one substantially cylindrical portion thereof having longitudinal development axis substantially coinciding with the longitudinal development axis of the portion of vessel 5 to be treated.

Figure 10:
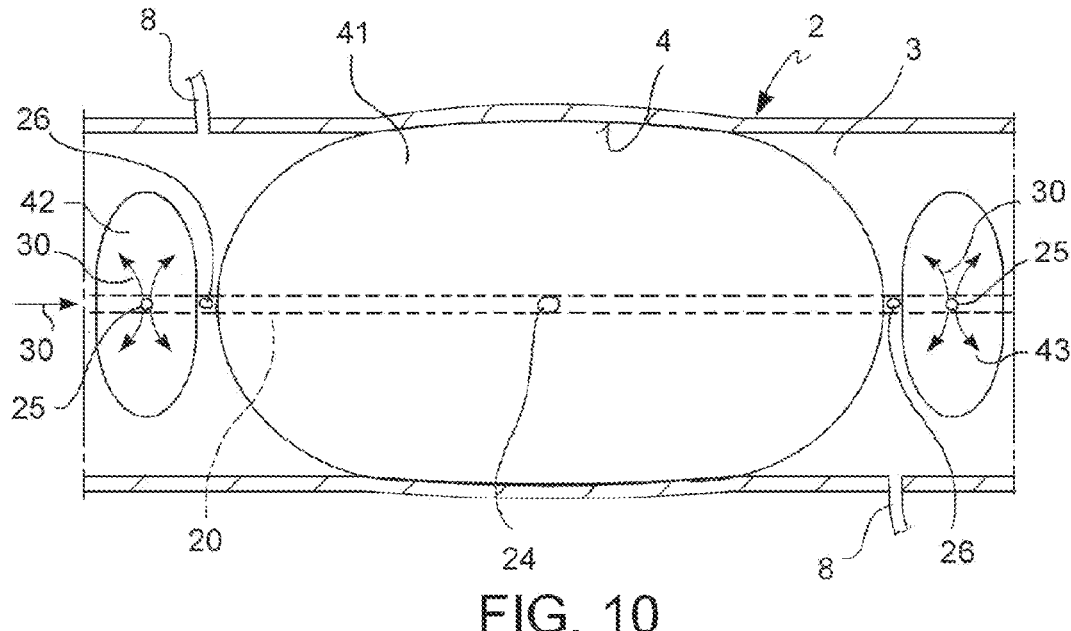
FIG. 10 is a schematic longitudinal sectional view of a portion of a catheter shaft inside a blood vessel, according to an embodiment, during the expansion by inflation of an expandable balloon.

As shown for example in FIG. 10, due to the inflation of said at least one occlusion balloon 42, 43, and preferably at least two occlusion balloons 42, 43 longitudinally opposite to said core balloon 41, a vessel segment 5 to be treated is temporarily isolated from the circulatory system. The occlusion balloons 42, 43 are preferably expanded radially after the core balloon 41 has assumed its maximum radial expansion and in this way has emptied the vessel segment 5 to be treated from the blood. The occlusion elements 42, 43 may be made expandable also in other ways, for example they may comprise umbrella structures.

Figure 8:
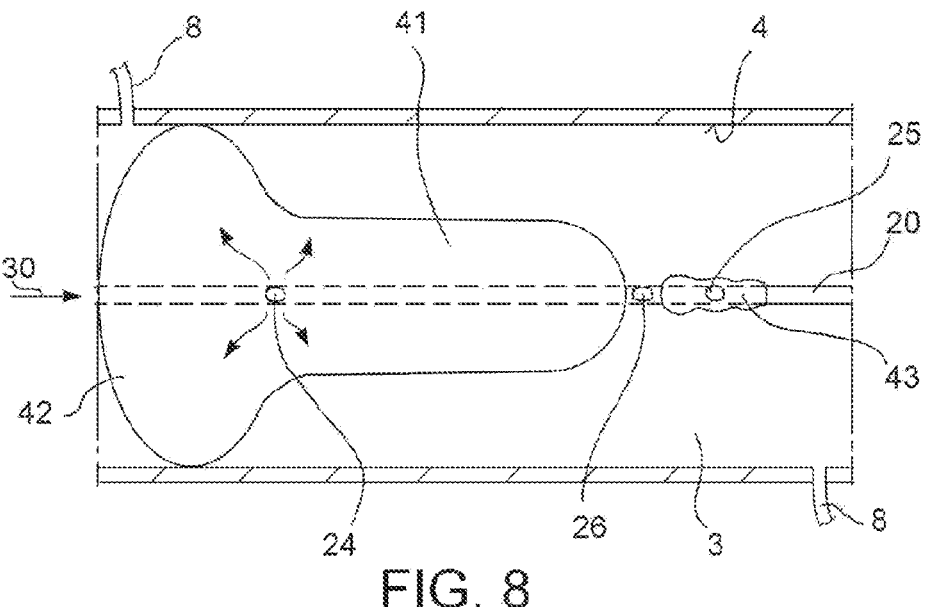
FIG. 8 is a schematic longitudinal sectional view of a portion of a catheter shaft inside a blood vessel, according to an embodiment which provides an expandable balloon which acts as a core made as a single piece with an expandable balloon which acts as an occlusion element, during the inflation of an expandable balloon.
Figure 9:
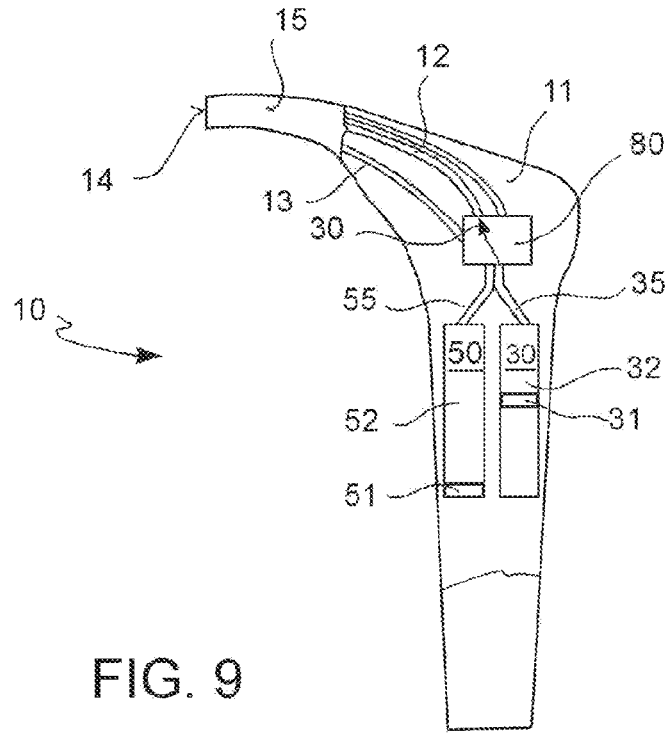
FIG. 9 is a schematic view with partially transparent parts, for clarity, of a catheter handle, according to an embodiment, during the inflation of at least one expandable balloon fitted onto an associable catheter shaft.

According to an embodiment shown for example in FIG. 8, said core balloon 41 is made in a single piece with an occlusion balloon 42 or 43. In this way, the occlusion balloon 42 or 43 made in one piece with said core balloon 41 is inflated first, and after the core balloon 41, and subsequently the other occlusion balloon 43 or 42.

Due to the provision of said synchronization device 60, the vascular catheter 1 is able to synchronize the volume of pharmacological fluid 50 delivered towards said second portion 44 of the isolated volume 40 with the volume of first fluid 30 taken by said expandable balloon 41 which acts as a core, keeping the paths of the first fluid 30 and the second fluid 50 independent, and allowing the size of the isolated volume 40 to be adjusted if necessary, making the catheter shaft repositionable in various portions of the blood vessel 2 having different caliber.

Preferably, the first hole 24 and the second hole 26 belong to distinct catheter paths 11, 12 which are separated from each other, for example by partitions, along the entire longitudinal extension of the vascular catheter 1. The partitions may be substantially concentric with each other, or directed substantially radially in the cross section of said vascular catheter 1.

According to an embodiment, at least some of said handle paths 11, 12, 13 lead into a selector device 80 which can preferably be placed in the catheter handle 10.

According to a preferred embodiment, when said synchronization device 60 is operatively connected to both said first pumping device 31 and said second pumping device 51, said catheter handle 10 delivers a predetermined volume of pharmacological fluid 50 and automatically simultaneously takes an equal predetermined volume of first fluid 30.

The provision of such a synchronization device 60 allows, if necessary, for example at the end of the pharmacological treatment, to withdraw, i.e. recover, a predetermined volume of pharmacological fluid 50 from said predefined intra-vascular volume 40 and at the same time deliver an equal predetermined volume of first fluid 30 in the same predefined intra-vascular volume 40. In this way, it is possible to recover the pharmacological agent at the end of the treatment, without changing the pressure in said predefined intra-vascular volume 40. The recovered pharmacological fluid does not contaminate the at least one handle path 12, 13 intended for the transport of inflation fluid.

According to a preferred embodiment, when said synchronization device 60 is operatively connected to both said first pumping device 31 and said second pumping device 51, said catheter handle 10 supplies a predetermined volume of pharmacological fluid 50 and takes an equal predetermined volume of first fluid 30 by a single control action by an operator of the catheter handle 10, for example a surgeon.

Preferably, the term "single control action" is meant to indicate a single action performed by said operator on a control interface 61 of the catheter handle 10, such as for example a pressure action of a single key 61 or a single button 61 or a single control lever 61 or a rotation action of a control ring 61 by said operator. For example, said single control action is performed by an operator finger.

Preferably, the terminology "single control action" does not exclude that a train of control signals 79 transmitted by said control interface 61 to said synchronization device 60 and/or to at least one of said first pumping device 31 and said second pumping device 51 may be generated as an effect of the only control action performed by the operator on said control interface 61.

According to an embodiment, the synchronization device 60 is operably connectable to both said first pumping device 31 and to said second pumping device 51 through a drive interface 62, preferably placed on the casing 15 of the catheter handle 10, so that it is accessible to an operator, for example an operator while holding said catheter handle 10.

For example, said drive interface 62 comprises a key or button or a control lever or a control ring.

Due to said drive interface 62 it is possible to activate said synchronization device 60, operatively connecting it to both said first pumping device 31 and to said second pumping device 51.

The provision of such a vascular catheter 1 allows supplying the drug 50 and simultaneously taking an equal volume of first fluid 30, without thereby requiring a long training of at least one operator. In other words, due to the provision of such a catheter handle 10 comprising such a synchronization device 60, the functionality of the vascular catheter 1 described herein becomes independent of the operator's ability.

The simultaneous provision of a detection device comprising at least one sensor 27, 76, operatively connected to said synchronization device 60, for example by means of a control device 75, is particularly advantageous in automating the functionality of the catheter 1 described above, as will be detailed below.

According to an embodiment, said first pumping device 31 comprises at least one hydraulic pump, for example a micro-pump, with electric and/or pneumatic and/or mechanical activation. For example, said first pumping device 31 comprises at least one electromechanically actuated pump. According to an embodiment, said second pumping device 51 comprises at least one hydraulic pump, for example a micro-pump, with electric and/or pneumatic and/or mechanical activation. For example, said second pumping device 52 comprises at least one electromechanically actuated pump.

According to an embodiment, said first pumping device 31 comprises at least a first plunger 33 or piston 33, adapted to slide within a respective first tank 32 which comprises at least one cylinder 32 in fluid connection with at least one handle path 11, 12, 13. In this way, said first pumping device 31 and said first tank 32 cooperate forming a syringe, preferably a catheter syringe.

According to an embodiment, said second pumping device 51 comprises at least a second plunger 53 or piston 53, adapted to slide within a respective second tank 52 which comprises at least one cylinder 52 in fluid connection with at least one handle path 11, 12, 13. In this way, said second pumping device 51 and said second tank 52 cooperate forming a syringe, preferably a catheter syringe.

Preferably, said synchronization device 60 is adapted to couple, i.e. to make dependent on each other and preferably counter-dependent, the stroke of said first plunger 33 within said first tank 32 to the stroke of said second plunger 53 within said second tank 52.

According to an embodiment, said first pumping device 31 and/or said second pumping device 51 comprises a syringe pump. According to an embodiment, said first pumping device 31 and/or said second pumping device 51 comprises a reciprocating pump. According to an embodiment, said first pumping device 31 and/or said second pumping device 51 comprises a pressure generator.

Preferably, said first plunger 33 and said second plunger 53 are parallel to each other. In this way, the longitudinal development axis of said first plunger 33 is parallel to the longitudinal development axis of said second plunger 53. According to an embodiment, said first plunger 33 and said second plunger 53 are aligned with each other or mutually in axis. In other words, the longitudinal development axis of said first plunger 33 coincides with the longitudinal development axis of said second plunger 53 or a straight extension thereof.

According to a preferred embodiment, said synchronization device 60 is also adapted to decouple for at least a predefined stretch, in other words at least for a predefined free stroke the stroke of said first plunger 33 within said first tank 32 with the stroke of said second plunger 53 within said second tank 52. In this way, when under operating conditions, an overpressure is created inside the vessel segment 5 to be treated which prevents the blood contained in one or more collateral vessels 8, for example capillaries branching out from said vessel segment 5 to be treated, from flowing back into the interstice volume 44 of the lumen 3 of the vessel segment 5 to be treated.

Figure 17:
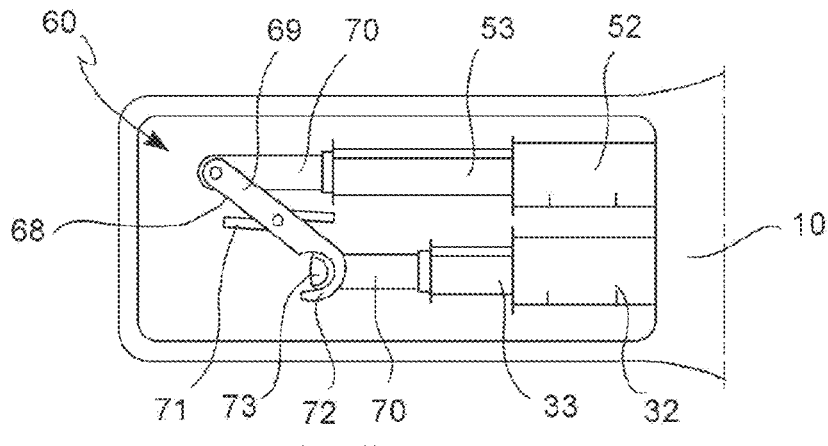
FIGS. 17 to 22 are schematic views with partially transparent parts, for clarity, of a catheter handle comprising a synchronization device, according to some embodiments.

According to an embodiment shown for example in FIG. 17, the body of said first plunger 33 and the body of said second plunger 53 are both associated with a leverage 68, comprising at least a rocker arm 69 pivoted to a portion of said catheter handle 10 and operatively connectable, directly or indirectly by interposing at least one connecting rod 70 of said leverage 68, to both the body of said first plunger 33 and the body of said second plunger 53, forming said synchronization device 60. In other words, said synchronization device 60 comprises said leverage 68 comprising said rocker arm 69 pivoted to a portion of said catheter handle 10. Preferably, said rocker arm 69 is slidably pivoted to a portion of said catheter handle 10, for example by means of a track 71. According to an embodiment, said rocker arm 69 of the synchronization device 60 comprises at least one cam portion 72, adapted to cooperate with a protuberance 73 integral with one between said first plunger 33 and said second plunger 53 to operate said synchronization device 60. According to an embodiment, said rocker arm 69 is associated with an elastic device for example placed in the fulcrum, and adapted to influence said rocker arm 69 so as to make said cam portion 72 to cooperate with said protuberance 73 which acts as a cam follower.

Such a synchronization mechanism allows, if necessary, due to the sizing of said track 71, to decouple the stroke of said first plunger 33 and of said second plunger 53 for a predefined length or idle stroke, so as to allow, for example, supplying the pharmacological agent 50 in advance with respect to the opposite suction of the first fluid 30 from the segment of the vessel 5 to be treated.

Figure 18:
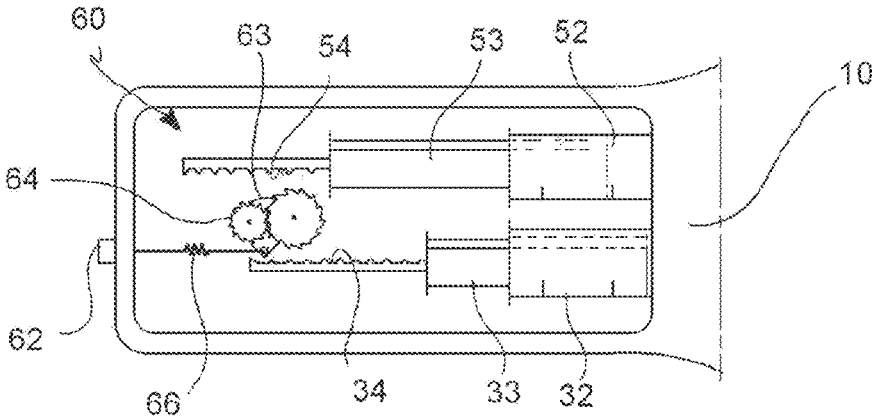
Figure 19:
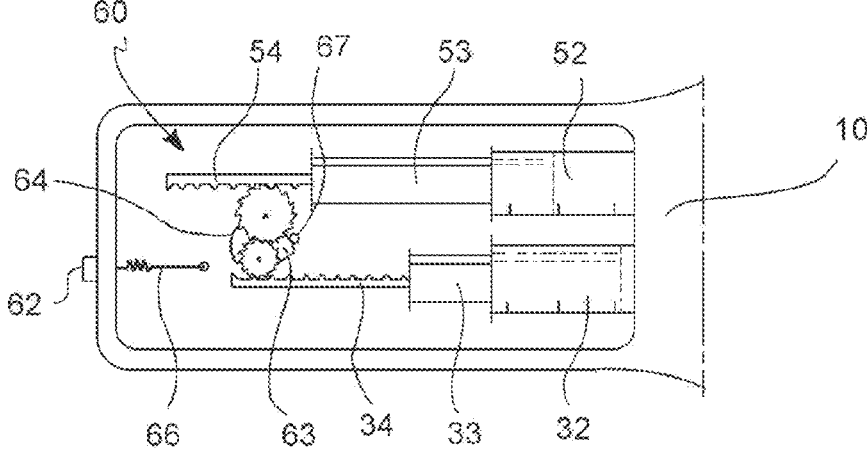

According to an embodiment shown for example in FIGS. 18-19, the body of said first plunger 33 comprises at least a first rack 34, preferably parallel to the longitudinal development axis of said first plunger 33, and the body of said second plunger 53 comprises at least a second rack 54, preferably parallel to the longitudinal development axis of said second plunger 53, wherein said synchronization device 60 further comprises at least one gear unit 64, for example a pair of toothed wheels meshed together for counter-rotating, wherein a first toothed wheel of said gear unit 64 is adapted to selectively mesh also said first rack 34 and a second toothed wheel of said gear 64 is adapted to selectively mesh also said second rack 54. In other words, said synchronization device 60 comprises said at least one gear unit 64 and said racks 35, 55 associated with respective plungers 33, 53 of said first and second pumping device 31, 51. According to an embodiment, said gear unit 64 is associated with a movable support 63, for example a plate hinged to the body of said catheter handle 10, wherein said movable support 63 is preferably adapted to move, when operated by means of said drive interface 62, within an operating position in which said gear unit 64 engages said racks 34, 54, and a rest operation, in which said gear unit and said racks 34, 54 are not in contact. Preferably, said at least one movable support 63 is influenced by an elastic device 66 towards said rest position and preferably by operating said drive interface 62 disengages said elastic device 66, ceasing the influence action. Preferably, a stop 67 is provided which acts as a limit switch for moving said movable support 63.

The provision of said gear unit 64 and of said racks 34, 54 allows implementing a synchronization device 60 which comprises a synchronization mechanism.

Due to the provision of the movable support 63 it is possible, if necessary, to decouple the stroke of said first plunger 33 and of said second plunger 53 for a predefined length or idle stroke, so as to allow, for example, supplying the pharmacological agent 50 in advance with respect to the opposite suction of the first fluid 30 from the segment of the vessel 5 to be treated.

Due to said drive interface 62, it is possible to control the actuation of said synchronization device 60, in other words it is possible to couple the stroke of said first plunger 33 and of said second plunger 53 on control.

Figures 20, 21, 22:
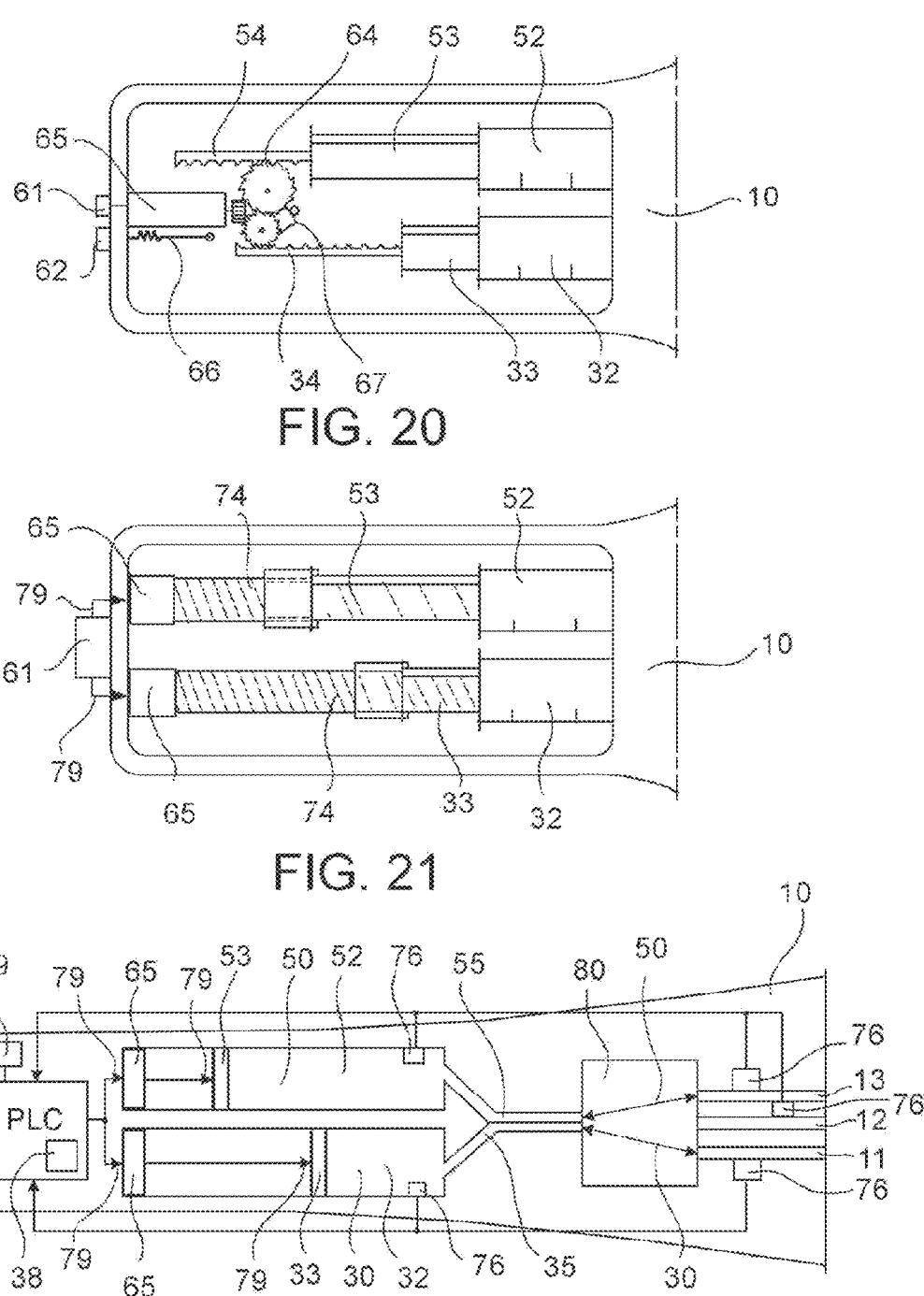

According to an embodiment shown for example in FIG. 20, said synchronization device 60 further comprises at least an electric motor 65 adapted to move said gear unit 64. Preferably, said electric motor 65 can be operated by said single control action by the operator and is operatively connected to said control interface 61.

According to an embodiment, said synchronization device 60 comprises at least one screw-nut assembly 74 operatively connected to at least one of said first plunger 33 and said second plunger 53. The provision of said screw-nut assembly 74 allows implementing a synchronization device 60 which comprises a synchronization mechanism.

Preferably, as shown for example in FIG. 21, said synchronization device 60 comprises a pair of screw-nut assemblies 74, the nut or slider of each screw-nut assembly 74 being operatively connected to one between said first plunger 33 and said second plunger 53. For example, the screw of the at least one screw-nut assembly 74 is placed at a different level with respect to said tanks 32, 52, so as not to obstruct the movement path of said plungers 33, 53. Preferably, at least one electric motor 65 operable by said control interface 61 is associated with said at least one screw-nut assembly 74.

According to a variant, said synchronization device 60 is adapted to generate a pressure difference which determines the movement in the opposite direction of said plungers 33, 53. In this way, said synchronization device 60 comprises a pneumatic synchronization device.

According to an embodiment as shown for example in FIG. 22, said synchronization device 60 comprises a control device 75 comprising at least one programmable logic controller or PLC which cooperates with at least one electric motor 65. Preferably, said control device 75 further comprises an actuation device. Preferably, said control device 75 further comprises a data processing unit. Preferably, said control device 75 further comprises a memory 38. In this way, said synchronization device 60 can comprise a synchronization algorithm.

According to an embodiment, the catheter handle 10 further comprises at least one power supply 39, operatively connected to said synchronization device 60. For example, said power supply 39 is operatively connected to said electric motor 65. Preferably, said power supply 39 comprises at least one battery 39, for example a low voltage battery. According to an embodiment, said catheter handle 10 comprises at least one sealed chamber which receives at least one of: said power supply 39, for example a battery, said programmable logic controller of said control device 75, said electric motor 65. According to an embodiment, said at least one sealed chamber also receives other components of the control device 75.

According to an embodiment, said synchronization device 60 comprises a control device 75 comprising at least one programmable logic controller or PLC which cooperates with at least one electric motor 65 operatively connected to at least one of, and preferably both, said first pumping device 31 and said second pumping device 32.

According to an embodiment, said control device 75 cooperates with a sensing device comprising at least one handle sensor 76, adapted to detect information on the state of the fluid 30 or 50 within at least one path of said at least two handle paths 11, 12, 13, for example within the handle 10. Preferably, the control device 75 transmits control signals 79 to said at least one electric motor 65 on the basis of the processing of the information detected by said sensing device. Preferably, said at least one handle sensor 76 comprises at least one pressure sensor 76 adapted to detect pressure information inside at least one of said at least two handle paths 11, 12, 13. Preferably, said at least one handle sensor 76 comprises at least one flow meter 76 adapted to detect information on the fluid flow within at least one of said at least two handle paths 11, 12, 13.

According to an embodiment, the control device 75 can be actuated by means of said control interface 61, so as to transmit control signals 79 to said electric motor 67.

According to an embodiment, at least one of said first tank 32 and said second tank 52 is a sealed chamber made inside the casing 15 of the catheter handle 10.

Not necessarily said first tank 32 and said second tank 52 have the same cross-sectional area on which said associated plunger 33, 53 rests, even though according to a preferred embodiment they do. The provision of said synchronization device 60 in fact allows acting on the predetermined volume of pharmacological fluid 50 supplied and on the equal predetermined volume of first fluid 30 withdrawn. In other words, the synchronization device 60 determines a flow rate of pharmacological fluid 50 and an equal flow rate of first fluid 30.

According to an embodiment, said synchronization device 60 acts by coupling the stroke of the plungers 33, 53, and in the case in which said first tank 32 and said second tank 52 have the same cross-sectional area on which said associated respective plungers 33, 53 rest, then the synchronization device 60 determines a movement at the same speed and in the opposite direction of said two plungers 33, 53 with respect to the respective associated tanks 32, 52.

According to an embodiment, said at least two handle paths 11, 12, 13 are at least three handle paths 11, 12, 13 and preferably, a core balloon handle path 11 is fluidly connected with at least a first hole 24 which opens into said at least one expandable core balloon 41. Preferably, an interstitial handle path 11 is fluidly connected with a second hole 26 which opens into the isolated volume 40 outside the core balloon 41, in other words in said second portion 44 of the isolated volume 40.

According to an embodiment, an occlusion balloon handle path 12 is fluidly connected with at least a third shaft hole 25 which opens into said at least one occlusion balloon 42, 43, when the occlusion elements are made in the form of expandable balloons.

According to a preferred embodiment, not necessarily combinable with the embodiments shown herein, said catheter handle 10 comprises a selector device 80 in fluid connection, directly or indirectly by means of a first pumping device 31, both with said first tank 32 and with said at least two handle paths 11, 12, 13, said selector device 80 being adapted to temporarily occlude at least one handle path 11 or 12 or 13 of said at least two handle paths 11, 12, 13 at a time. If necessary, said selector device 80 is adapted to simultaneously open all the handle paths 11, 12, 13 which is capable of occluding, such as for example during the simultaneous emptying of said core balloon 41, of at least one occlusion balloon 42, 43 and of said second portion 44 of the isolated volume 40 of the segment 5 to be treated of blood vessel 2. Preferably, said selector device 80 is in fluid communication also with said second tank 52.

According to an embodiment, said selector device 80 is operatively connected to a selector activation interface 81, preferably comprising a selector activation element adapted to determine the mode of operation of the selector device 80. In other words, said selector device 80 can be operated by means of a selector activation interface 81, such as for example a control ring 81 adapted to be switched to a plurality of operating positions, and/or a control switch 81, and/or a control button 81.

According to an embodiment, said first tank 32 is in fluid communication with a first tank conduit 35 and said second tank 52 is in fluid communication with a second tank conduit 55, distinct from the first tank conduit 35, and wherein said first tank conduit 35 and said second tank conduit 55 lead into said selector device 80.

According to an embodiment, said selector device 80 is adapted to lead into at least one of said at least three handle paths 11, 12, 13. Preferably, said selector device 80 is adapted to flow, if necessary, into each and all of the at least three handle paths 11, 12, 13. For example, at the end of the treatment of the vessel segment 5 to be treated, all the expandable balloons 41, 42, 43 are emptied of the first fluid 30, preferably inflation fluid 30, and preferably but not necessarily simultaneously, the interstitial volume 44 is also emptied from the pharmacological fluid 50.

According to an embodiment, said selector device 80 comprises at least a first valve 81, adapted to occlude at least one of: said core balloon handle path 11 and said occlusion balloon handle path 12.

Figures 11, 12:
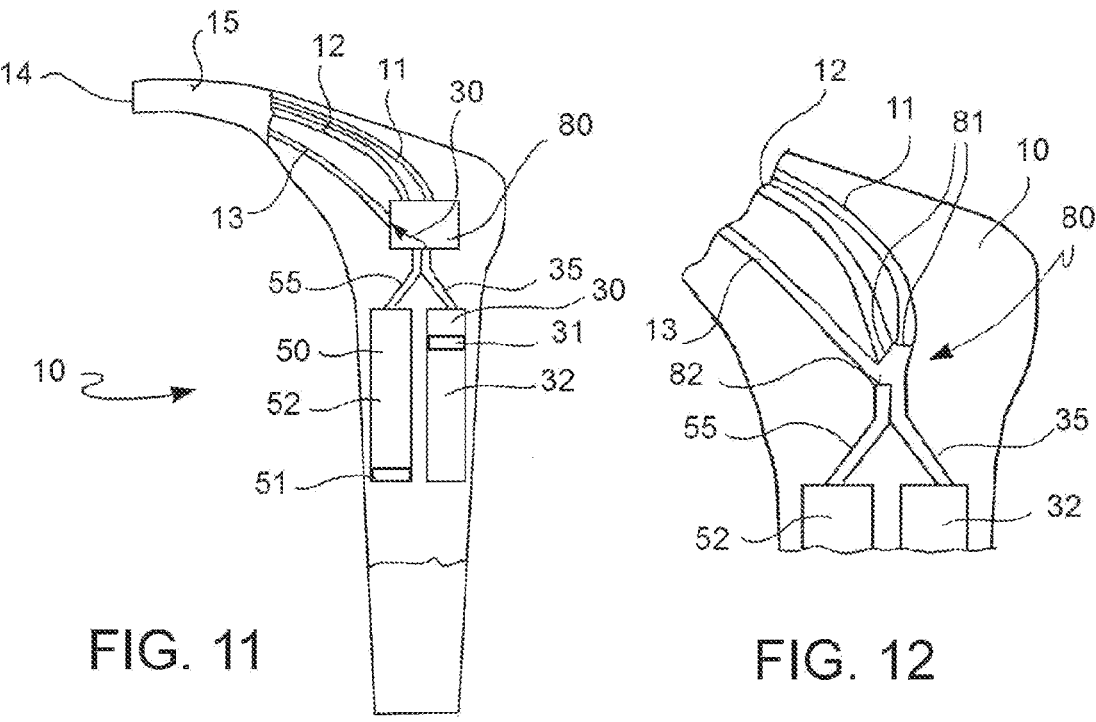
FIG. 11 is a schematic view with partially transparent parts, for clarity, of a catheter handle, according to an embodiment, during the delivery of the first fluid in an expandable balloon in an isolated volume.
FIG. 12 is an enlarged view of a detail of FIG. 11, which shows a selector device according to an embodiment.
Figure 13:
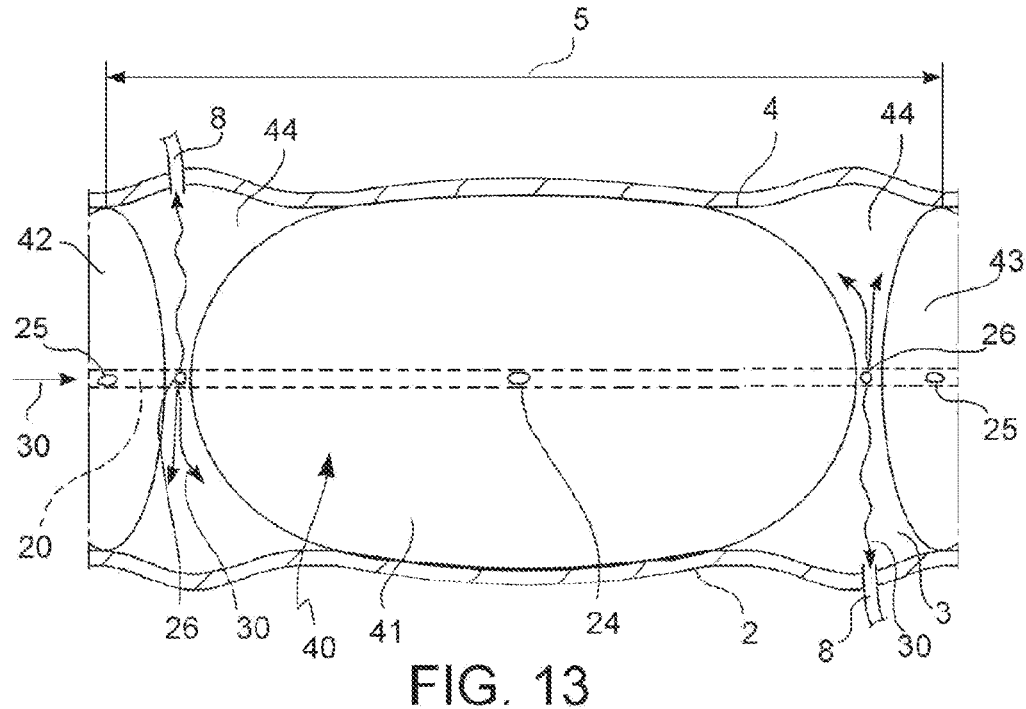
FIG. 13 is a schematic longitudinal sectional view of a portion of a catheter shaft inside a lumen, according to an embodiment, during the delivery of the first fluid in an expandable balloon in an isolated volume.
Figures 14, 15:
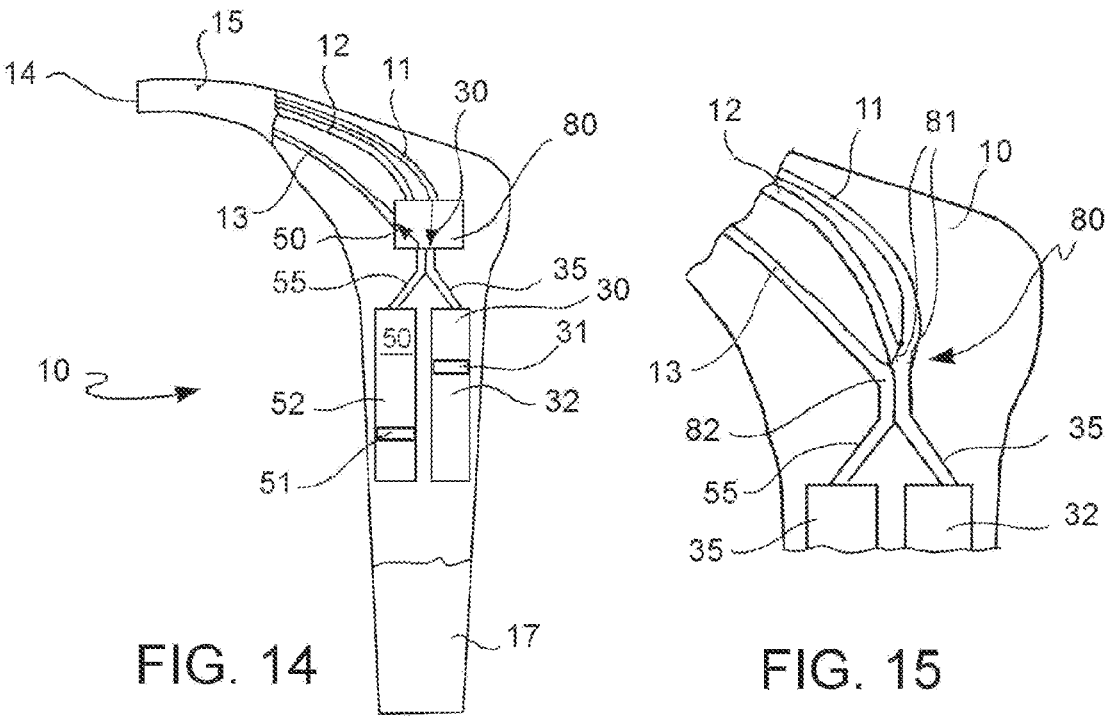
FIG. 14 is a schematic view with partially transparent parts, for clarity, of a catheter handle, according to an embodiment, during the delivery of a second fluid in an isolated volume portion and the simultaneous suction of the first fluid from an expandable balloon in the isolated volume.
FIG. 15 is an enlarged view of a detail of FIG. 14, which shows a selector device according to an embodiment.
Figure 16:
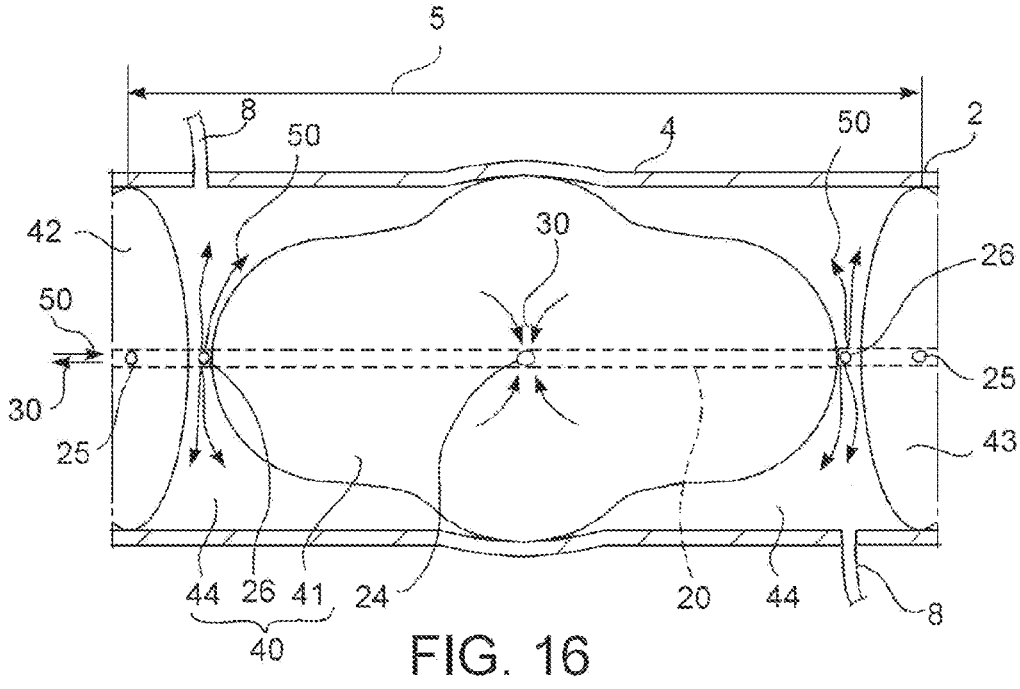
FIG. 16 is a schematic longitudinal sectional view of a portion of a catheter shaft inside a blood vessel, according to an embodiment, during the delivery of a second fluid in an isolated volume portion and the simultaneous suction of first fluid from an expandable balloon in an isolated volume.

According to an embodiment as shown for example in FIG. 12, said selector device 80 comprises two first valves 81, a first valve 81 being adapted to selectively occlude said core balloon handle path 11 and the other first valve 81 being adapted to selectively occlude the occlusion balloon handle path 12.

According to an embodiment as shown for example in FIG. 22, said selector device 80 is adapted to simultaneously place in fluid communication said first tank 32 with said core balloon handle path 11, and said second tank 52 with said interstice handle path 13.

According to an embodiment, said selector device 80 comprises at least a second valve 82, adapted to selectively place in fluid communication said first tank 32 with said interstice handle path 13.

According to an embodiment, at least one of said at least one first valve 81 and said second valve 82 comprises at least one non-return valve. According to an embodiment, at least one of said at least one first valve 81 and said second valve 82 comprises at least one solenoid valve. Preferably, said solenoid valve is associated with a control device 75. Preferably, the control device 75 is associated with a detection device comprising at least one handle sensor 76, so that said control device 75 is adapted to transmit control signals 79 to said selector device 80 on the basis of the processing of the information detected by said detection device.

According to an embodiment, said detection device comprises at least one shaft sensor 27.

According to an embodiment, the catheter 1 and preferably the catheter handle 10 comprises at least one indicator, for example a display 77, adapted to display information detected by said detection device. Preferably, said indicator, for example a display 77 is operatively connected with said control device 75. Preferably, said indicator, for example a display 77, is placed on said casing 15 of the catheter handle 10 so as to be visible to the operator when handling or holding said catheter handle 10. For example, said indicator, for example a display 77 is adapted to display information on the pressure of the first fluid 30 inside the catheter handle 10 as for example in said first tank conduit 35. For example, the information on the pressure of the first fluid 30 when acting as the inflation fluid of at least one expandable balloon indirectly contains information on the state of the balloon such as for example information on the elasticity of the wall 45 of the expandable balloon. For example, said indicator, for example a display 77 is adapted to display information on the flow rate of the first fluid 30 inside the vascular catheter 1, such as for example in said core balloon handle path 41.

According to an embodiment, the casing 15 of said catheter handle 10 comprises a window 16 adapted to allow the operator a visual inspection of at least one of: said first tank 32 and said second tank 52. For example, said window 16 is made of material transparent to visible light.

According to a preferred embodiment, not necessarily combinable with the above embodiments, said catheter shaft 20 is associated with a detection device comprising at least one catheter sensor 27, adapted to detect information on the state of said at least one expandable balloon 41, 42, 43 fitted onto said catheter shaft 20 at a shaft opening 24 or 25.

Preferably, an indicator, for example a display 77 provided on the casing 15 of the catheter handle 10 is operatively connected to said detection device to display the information detected on the state of said at least one catheter balloon 41, 42, 43 fitted onto said catheter shaft 20 at a shaft opening 24 or 25.

According to an embodiment, said at least one catheter sensor 27 is adapted to detect information on the state of the expandable balloon 41, preferably when the balloon wall 45 is in contact with said vessel wall 4 of said vessel segment 5 to be treated.

According to a preferred embodiment, said at least one catheter sensor 27 comprises at least one pressure sensor 27, adapted to detect information on the pressure of the first fluid 30 inside said expandable balloon. Preferably, said at least one pressure sensor 27 is placed in the proximity or at a first hole 24 of said catheter shaft 20 which opens into said expandable core balloon 41. Preferably, said at least one handle sensor 76 comprising at least one pressure sensor 76, adapted to detect pressure information within at least one path of said at least two handle paths 11, 12, 13 is adapted to detect the pressure inside the expandable balloon in fluid communication with at least one path of said at least three handle paths 11, 12, 13.

Due to the provision of said at least one pressure sensor 76 provided on the catheter handle 10 and/or of at least one pressure sensor 27 associated with the catheter shaft 20, it is possible to control the inflation operation of said at least one expandable balloon 41 as well as occlusion elements when made in the form of expandable balloons. In this way, it is possible to obtain a controlled over-inflation of the core balloon 41. Preferably, the term "over-inflation" means an inflation of the balloon which generates an over-extension or over-elongation of the wall 4 of the blood vessel 2, generating the breakage of the cellular bonds of the inner layer 6 of the wall 4 of the blood vessel 2. Inducing controlled over-inflation of the core balloon 41 allows generating micro-lesions 9 or lesions 9 in the innermost layer 6 or endothelial layer 6, comprising endothelial cells, of the vessel wall 4 of said vessel segment 5 to be treated. These micro-lesions 9 form passage channels 9 for the pharmacological fluid 50 which allow the penetration of the pharmacological agent into at least one muscle layer 7 or muscular tunic 7, comprising muscle cells, of the vessel wall 4 of said vessel segment 5 to be treated, avoiding to tear or damage an additional outer layer 78 of the wall 4 of the blood vessel 2, called adventitious tunic 78, which could generate bleeding.

Due to the provision of said at least one catheter sensor 27 and/or said handle sensor 76, for example a pressure sensor 27 or 76 placed in fluid communication with the inside of the expandable core balloon 41, it is possible to control the over-inflation of said balloon. In other words, the breakage of the intercellular bonds of the inner layer 6 due to the over-extension of the vessel wall 4 increases the permeability of the vessel wall 4 and promotes the penetration of the pharmacological agent into the thickness of the vessel wall 4, so as to obtain an increased therapeutic effect.

According to an embodiment, said at least one catheter sensor 27 comprises at least one flow meter 27, adapted to detect information on the flow entering into or exiting from said balloon 41. Preferably, said at least one flow meter 27 is placed in the proximity or at an opening 24 of said catheter shaft 20 which opens into said core balloon 41.

Figure 2:
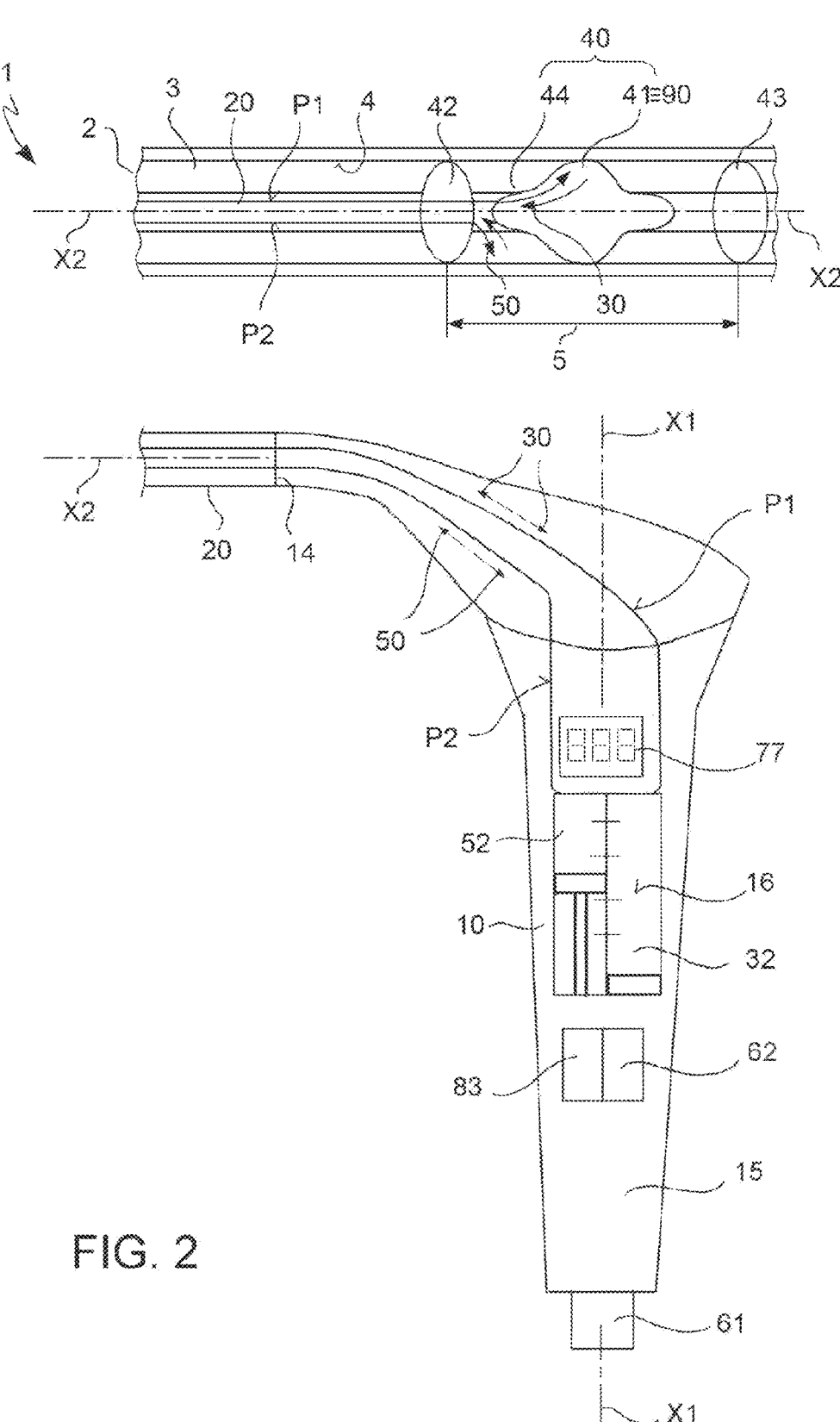
FIG. 2 shows a schematic view of a vascular catheter, according to an embodiment.
Figure 3:
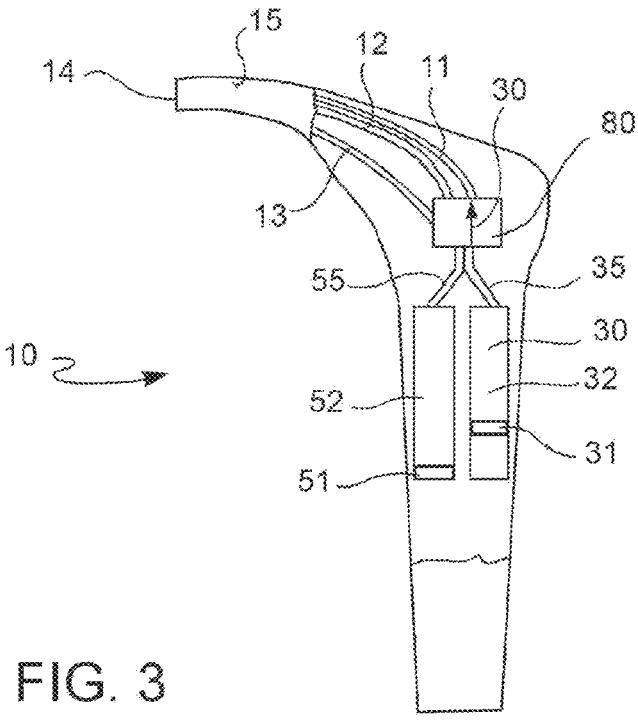
FIG. 3 is a schematic view with partially transparent parts, for clarity, of a catheter handle, according to an embodiment, during the inflation of an expandable balloon fitted onto an associable catheter shaft.
Figure 4:
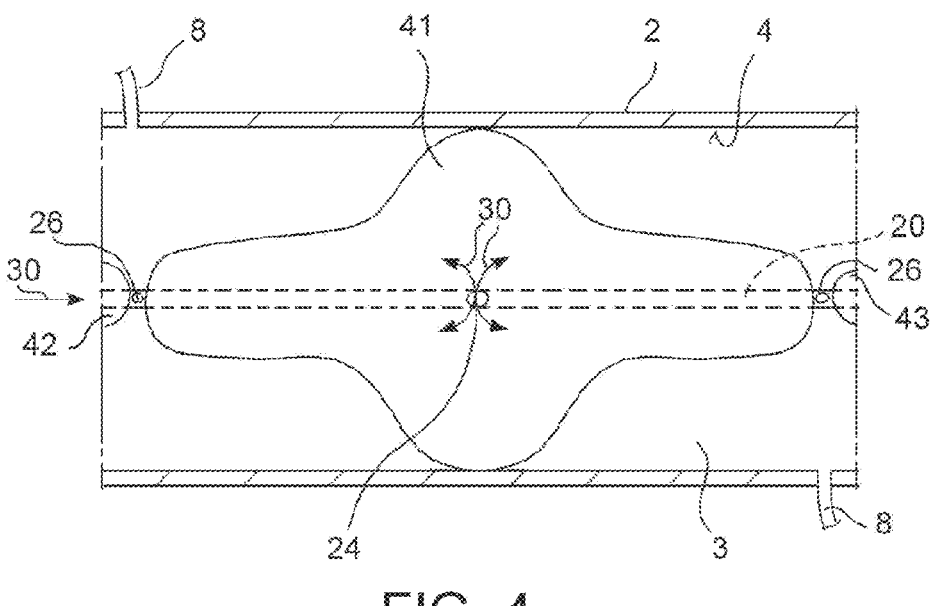
FIG. 4 is a schematic longitudinal sectional view of a portion of a catheter shaft inside a blood vessel, according to an embodiment, during the inflation of an expandable balloon.
Figure 5:
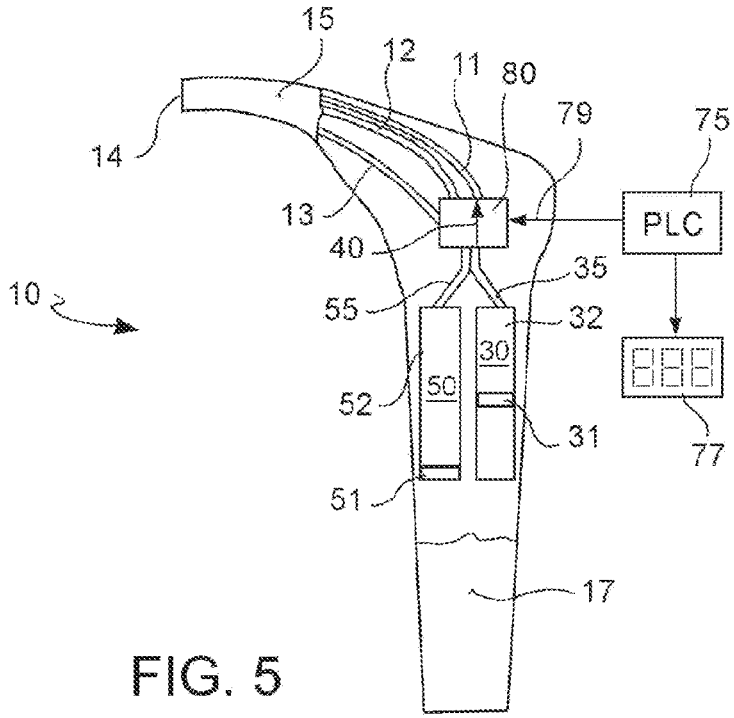
FIG. 5 is a schematic view with partially transparent parts, for clarity, of a catheter handle, according to an embodiment, during the inflation of an expandable balloon fitted onto an associable catheter shaft, wherein a control device associated with said catheter handle is also diagrammatically depicted.

According to an embodiment as shown for example in FIGS. 5 and 6, said at least one catheter sensor 27 is operatively connected with said control device 75, adapted to transmit control signals 79 to said selector device 80 on the basis of processing of the information detected by said at least one catheter sensor 27. For example, said at least one catheter sensor 27 detects information on the first fluid 30, preferably inflation fluid, and transmits it to said control device 75 which compares said information on the state of said balloon 41 as well as of said occlusion elements 42, 43 when made in the form of expandable balloons with at least one reference value, for example stored in said memory 38, and if said information on the state of said at least one balloon is incompatible with the reference value, it transmits control signals 79 to said selector device 80 for selectively occluding or opening at least one handle path 11, 12, 13.

Preferably, said selector device 80 comprises at least one shutter body 81 or 82, and preferably a plurality of shutter bodies 81, 82, each adapted to selectively occlude at least one handle path 11, 12, 13 of said at least three handle paths 11, 12, 13 at a time. According to an embodiment, said indicator, for example a display 77 is adapted to display information detected by said at least one catheter sensor 27 and/or said at least one handle sensor 76.

According to a preferred embodiment, not necessarily combinable with one or more embodiments reported herein, the longitudinal development direction of said catheter handle X1-X1, and preferably of said handle 17 of the catheter handle 10, is directed transversely to the longitudinal development direction of said catheter shaft X2-X2.

This allows improved ergonomics for the operator.

Preferably, the longitudinal development direction of said catheter handle X1-X1 forms an angle 19 with respect to the longitudinal direction of said catheter shaft X2-X2, and preferably said angle 19 is comprised between 30° and 150°, and even more preferably it is comprised between 60° and 120°. According to a preferred embodiment, said angle 19 is substantially 90°.

According to an embodiment, said catheter 1 has the catheter shaft 20 orientable with respect to the catheter handle 10 in various directions and not necessarily said catheter 1 is a vascular catheter.

According to an embodiment, said catheter handle 10 is associated with a cap 84. According to a preferred embodiment, said cap 84 comprises a distal cap opening 85 adapted to be crossed by a portion of said catheter shaft 20, when said catheter shaft 20 is operatively connected to said catheter handle 10. Preferably, said cap 84 is associated with the body of said catheter handle 10 so as to be able to rotate with respect to said catheter handle body 10 along a direction of rotation R1. For example, said cap 84 can be rotated about an axis coincident or parallel to the longitudinal development axis X1-X1 of said catheter handle 10. Preferably, said cap 84 further comprises a proximal cap opening 88, opposite to said distal cap opening 85 with respect to the body of said cap 84.

Preferably, said proximal cap opening 88 and said distal cap opening 85 are offset from each other. In this way, the shaft direction X2-X2 evaluated in the proximity or at said proximal cap opening 88 is not coincident with the longitudinal direction X2-X2 evaluated in the proximity or at said distal cap opening 85. For example, said cap 84 is fitted coaxially on said catheter handle 10 and is associated with the proximal end 14 of the catheter shaft 20.

According to an embodiment, said proximal cap opening 88 is facing in the longitudinal handle direction X1-X1, and said distal catheter opening 85 is facing in said longitudinal catheter direction X2-X2.

The provision of said cap 84 allows making a catheter handle 10 having an adjustable head. In this way, it is possible to modify, if necessary, the orientation of the catheter shaft 20 with respect to the catheter handle 10. In this way, an operator, typically a surgeon, is allowed to operate with improved comfort compared to known solutions, in that he/she is able to rotate the cap 84 if necessary, causing a change in the relative orientation between the catheter handle 10 and the catheter shaft 20, without thereby leading to alterations of the handle paths 11, 12, 13.

At the same time, right-handed and left-handed operators are allowed to operate in the same conditions. In this way, an improved repeatability of the treatment is allowed.

According to an embodiment, the body of said cap 84 at least partially delimits a cap compartment 89, said cap compartment 89 receiving a proximal portion of said catheter shaft 20 which forms a shaft curve 18. Preferably, said shaft curve 18 forms a connection between said connection interface 14 of the catheter handle 10 and said distal cap opening 85.

According to an embodiment, said cap 84 comprises at least one engagement portion 86 which engages with an engagement counter-portion 87 of said catheter handle 10. Preferably, said engagement portion 86 is placed on the edge of said proximal cap opening 88 and said engagement counter-portion 87 is placed on the casing 15 of the catheter handle 10. According to an embodiment, one between said engagement portion 86 and said engagement counter-portion 87 comprises a guide, preferably an annular guide, and the other between said engagement portion 86 and said engagement counter-portion 87 comprises at least one contact element, comprising an undercut portion adapted to abut against a reciprocal portion of said guide when said cap 84 is moved away from said catheter handle 10. According to an embodiment, said engagement portion 86 and said engagement counter-portion 87 engage with each other by snap-fit. For example, a portion of the cap 84 disposed on the edge of said proximal cap opening 88 is elastically deformable when the cap 84 is pressed on the body of the catheter handle 10 to snap-fit against an undercut portion of said body of the catheter handle 10.

Due to such a catheter handle 10, the functionality of the vascular catheter 1 is made independent of the operator. For example, due to the provision of said cap 84, an operator is allowed to grasp the catheter handle 10 ergonomically under operating conditions when the catheter shaft 20 is inserted into a patient's blood vessel 2. For example, such a catheter handle 10 allows operating with the same comfort for the operator both when the shaft curve 18 is facing to his right 2, and when the shaft curve 18 is facing to his left.

A method of handling a catheter 1 will be described below.

A method of handling a catheter 1 provided with at least one balloon 41, 42, 43 fitted onto a catheter shaft 20 of said catheter 1 comprises the steps listed below.

The method comprises the step of providing a catheter 1, comprising a catheter handle 10 and a catheter shaft 20.

Preferably, said catheter handle 10 comprises at least one pumping device 31 which can be associated with at least one respective tank 32, containing a first fluid 30 for inflating and deflating at least one expandable balloon 41, 42, 43 fitted onto said catheter shaft 20 at a shaft opening 24 or 25.

According to a possible operating mode, the method comprises the step of providing a catheter handle 10 according to any one of the embodiments described above.

The method comprises the step of dispensing said first fluid 30 inside said at least one catheter balloon 41, 42, 43 by means of said pumping device 31, inflating the at least one balloon 41, 42, 43. In this way, said at least one balloon 41, 42, 43 is expanded at least radially and preferably both radially and longitudinally. Preferably, said at least one catheter balloon 41, 42, 43 is at least one core balloon 41. For example, as shown in FIG. 8, said at least one balloon comprises both a core balloon 41 and an occlusion balloon 42, 43.

According to a preferred operating mode, the method comprises the step of bringing the wall 45 of the balloon 41, 42, 43 into contact with the vessel wall 4 of the blood vessel 2. Preferably, the method comprises the step of bringing the wall 45 of the core balloon 41 into contact with the vessel wall 4 of the blood vessel 2.

According to a preferred operating mode, the method comprises the step of continuing to supply said first fluid 30 inside said at least one catheter balloon 41, 42, 43 by means of said pumping device 31, causing an over-inflation of the at least one expandable core balloon 41. Due to said over-inflation, it is possible to create on the vessel wall 4 a series of lesions 9 of the layer of vessel wall facing the lumen 3 of said blood vessel 2, so as to allow the pharmacological fluid 50 to soak at least one deep layer of the vessel wall 4, such as a layer consisting of muscle cells 7. In this way, an increased efficacy of the pharmacological fluid 50 is provided, under the same conditions of administration.

Preferably, the step of continuing to supply is carried out after the step of bringing the wall 45 of the expandable balloon 41 into contact with the wall 4 of the blood vessel 2. In this way, during the step of continuing to supply, the wall 45 of the expandable balloon 41 is in contact with the wall 4 of the blood vessel 2. In this way, the balloon wall transmits an action aimed at over-extending the wall 4 of the blood vessel 2.

When the wall 45 of the balloon 41 is brought into contact with the wall 4 of the blood vessel 2, and it continues to supply fluid 30 inside the balloon 41, the rate of increase in the volume of the balloon 41 decreases, and consequently the pressure increase rate increases.

According to a preferred operating mode, the method comprises the step of monitoring the state, preferably the stress and/or deformation state, of said expandable balloon 41.

According to a possible operating mode, this monitoring step is carried out by means of at least one catheter sensor 27. According to a preferred operating mode, this monitoring step is performed by at least one handle sensor 76. Preferably, said at least one handle sensor 76 comprises at least one pressure sensor 76. Preferably, said at least one pressure sensor 76 is placed on the catheter path 11 which opens into said core balloon 41 by means of said at least a first opening 24.

Preferably, said handle sensor 76 is operatively connected to at least one memory 38, adapted to store information on the state of said balloon detected by said at least one handle sensor 76 at predefined instants of time during the steps of the method. Preferably, said memory 38 is associated with said control device 75. In this way, the control device 75 records the variation over time of the pressure increase rate, and consequently of volume, inside said one expandable balloon 41, 42, 43. In this way, it is possible to monitor the over-inflation of the expandable balloon 41, 42, 43, while allowing to control it and therefore it is possible to obtain a qualitative control on the extent, for example the depth, of the lesions 9 induced on the inner layer 6 of the wall 4 of the blood vessel 2.

According to a possible operating mode, the control device 75 activates said indicator, for example a display 77, so as to signal to the operator the status of the balloon 41, 42, 43. According to a possible operating mode, said control device 75 activates said indicator, comprising a sound indicator, adapted to emit an acoustic signal to signal that the expected over-inflation has occurred.

Preferably, said control device 75 automatically transmits control signals 79, for example stop, to the first pumping device 31 on the basis of the information stored in said memory 38 and processed by said control device 75.

The monitoring step can be performed at any time the method.

According to a preferred operating mode, the monitoring step is performed simultaneously at least with the steps of bringing the wall 45 of the balloon 41 into contact with the wall 4 of the blood vessel 2 and of continuing the supply.

According to a preferred operating mode, the monitoring step is carried out simultaneously at least with the step of continuing the supply.

Due to the monitoring step, it is possible to control the over-inflation of the core balloon 41, so as to be able to control the extent of the lesions of the vessel wall 4, and preferably of the endothelial layer 6 of the vessel wall 4, generated by the controlled over-inflation of the core balloon 41. In particular, due to the provision of the monitoring step, it is avoided to generate lesions in the adventitious tunic 78, which lesions would cause the vessel segment 5 to be treated to bleed. At the same time, due to the monitoring step, the breaking of the wall 45 of the expandable balloon 41 is avoided.

For example, during the inflation of the expandable balloon 41, the pressure in the balloon 41 will change according to a pressure increase curve correlated to the variation of the caliber of the vessel 2, and during the expansion of the balloon 41 there will be in the initial step a relatively low increase in the pressure to then increase as the volume of the balloon 41 increases, when then the wall 45 of the balloon is brought into contact with the wall 4 of the vessel 4, for example a vein, there will initially be only a negligible increase in pressure due to the modest resistance of the wall 4 of the vessel 2 not yet dilated and radially stressed. In this way, due to the step of continuing to supply, a further increase in the volume of the balloon 41, and in particular of the diameter of the balloon 41, and therefore of the caliber of the vessel 2, will lead to a surge in the pressure value. In this step, the cellular bonds 9 of the inner layer 6 will break. Due to the pressure behavior, the device is capable of predicting the breaking moment of the wall 4 of the vessel 2 since the behavior of the pressure curve is independent of the initial caliber of the vessel 2, for example a vein. The provision of said at least one handle sensor 76, therefore, which cooperates with said control device 75, allows predicting, by analyzing the pressure curve stored by said memory 38, the breaking of the bonds both in vessels 2, for example veins, of 4 millimeters or "mm" of caliber or diameter, and in vessels 2, for example veins, of 20 mm of caliber or diameter.

According to a possible operating mode, the steps described above are all performed with at least a portion of said catheter 1 located inside the lumen 3 of a blood vessel 2.

According to a possible operating mode, the steps described above are all controlled by means of a catheter handle 10 of a vascular catheter 1 according to any one of the embodiments described above.

According to a possible operating mode, the method comprises the further step of dispensing said first fluid 30 inside said at least one occlusion balloon 42, 43, and preferably of both two occlusion balloons 42, 43 placed at longitudinal opposite sides with respect to said core balloon 41, by means of said pumping device 31, inflating the at least one occlusion balloon 42, 43. In this way, said at least one occlusion balloon 42, 43 is expanded at least radially, and preferably both radially and longitudinally, to form a sort of occlusion which, adhering to the vessel walls 4 along at least a cross section of said blood vessel 2, isolates the vessel section 5 to be treated from the circulatory system.

According to a preferred operating mode, the method comprises the further step of dispensing the first fluid 30, for example physiological solution, into the second portion 44 of the isolated volume 40, so as to remove the minimum residual blood content contained in the second portion 44 of the isolated volume 40 towards the collateral branches 8, which branch off from the wall 4 of the vessel segment 5 to be treated. This allows avoiding the contact of the proteins present in the blood with the pharmacological fluid 50 which will be delivered in this interstitial volume 44, since these proteins could be able to deactivate the pharmacological agent making the pharmacological treatment less effective. In this way, it is possible to increase the pressure in said interstitial volume 44, so that said pharmacological fluid penetrates at least into the mouth of one or more collateral vessels 8, for example capillaries, which branch off from the vessel wall 4 of the vessel segment 5 to be treated. In this way, said segment of the vessel 5 to be treated is emptied from the blood, before the supply of the pharmacological fluid 30, forming a physiological solution barrier between the drug in the interstitial volume 44 and the blood in the collateral vessels 8.

According to a preferred operating mode, the method comprises the further step of supplying drug in the second portion 44 of the isolated volume 40 between the walls 45 of at least one balloon 41, 42, 43 and the vessel wall 4 of a blood vessel segment 5 to be treated. According to a possible operating mode, this step is carried out by pressing a plunger 53 of a syringe. According to a possible operating mode, this step is performed by pressing a supply actuation control, preferably by means of a control interface located on the casing 15 of said catheter handle 10.

According to a possible operating mode, the method comprises the further step of deflating at least partially said at least one balloon 41, 42, 43. In other words, the method comprises the further step of contracting at least partially the volume of said at least one balloon 41, 42, 43, at least radially or radially. Preferably, this step of deflating at least partially said at least one balloon 41, 42, 43 provides for partially deflating the core balloon 41. According to a possible operating mode, this step is carried out by pulling a plunger 33 of a syringe. According to a possible operating mode, this step is performed by pressing a deflation actuation control, preferably by means of a control interface located on the casing 15 of said catheter handle 10.

Preferably, the drug supply step is carried out at the same time as the at least partially deflating the at least one balloon 41, 42, 43. In this way, the isolated volume 40 of said vessel segment 5 to be treated is kept substantially constant.

According to a possible operating mode, the method comprises the further step of synchronizing the volume of drug supplied in the second portion 44 of the isolated volume 40 with the volume of the first fluid 30 withdrawn from the expandable balloon 41 which acts as a core.

Due to the synchronization step, a balancing of the incoming and outgoing volumes of the isolated volume 40 is achieved which, while varying the share the isolated volume 40 occupied by the drug, allows for a fine volumetric adjustment, while determining that the drug is distributed in the proximity of the wall 4 of the vessel segment to be treated. It therefore makes it possible to reduce drug consumption for the same treatment efficacy. Synchronization can take place automatically or be controlled, i.e. activated, by an operator.

Preferably, the dispensing step and the deflating step are both performed simultaneously by means of a single control action.

According to a possible operating mode, said deflation actuation control and said supply actuation control may be activated automatically and simultaneously, by means of a single control action by an operator.

According to a possible operating mode, the synchronization step is performed after activating, or operating, a synchronization device 60 by means of a drive interface 62.

According to a possible operating mode, the drug supply step determines, when said synchronization device 60 is in operating conditions, the simultaneous activation of the deflation step of the core balloon 41.

For example, pressing said second plunger 53 causes the simultaneous movement in opposite direction of said first plunger 33. For example, by operating said second pumping device 51 the simultaneous actuation in opposite direction of said first pumping device 31 is determined.

According to a possible operating mode, the method further comprises the step of monitoring the supply of the drug and/or the deflation of the core balloon 41. Preferably, this step is performed by at least one flow meter 76.

The provision of said at least one flow meter 27, 76, and preferably at least one pair of flow meters 27, 76, of which at least one flow meter is placed in fluid communication with the second portion 44 of the isolated volume 40 and at least one flow meter is placed in fluid communication with said expandable core balloon 41, allows monitoring the flow rate of pharmacological fluid 50 supplied in the second portion 44 of the isolated volume 40 and the flow rate of the first fluid 30 withdrawn from said core balloon 41.

Preferably, the control device 75 processes the information on the flow rate acquired by said at least one flow meter 76, 27, and preferably by at least a pair of flow meters, to process it and transmit control signals to said synchronization device 60.

According to a possible operating mode, the step of supplying the drug is performed simultaneously with the step of at least partially deflating the expandable balloon 41 automatically, on the basis of information detected by a detection device and processed by a control device 75 which transmits control signals 79 to said synchronization device 60.

According to a possible operating mode, the monitoring step comprises the step of detecting the flow rate of the first fluid 30 leaving the expandable core balloon 41 which forms the first portion 90 of the isolated volume 40.

According to a possible operating mode, the monitoring step comprises the step of detecting the flow rate of pharmacological fluid 50 entering the second portion 44 of the isolated volume 40.

Preferably, the monitoring step is performed by comparing the flow rate of the first fluid 30 leaving the core balloon 41 with the flow rate of pharmacological fluid 50 entering the second portion 44 of the isolated volume 40.

According to a possible operating mode, before the drug supply step, the method provides the step of monitoring the pressure in the second portion 44 of the isolated volume 40. In this way, it is possible to deliver the drug by keeping a pressure in the dedicated catheter path slightly higher than the pressure of the second portion 44 of the isolated volume 40, avoiding the suction of blood or physiological solution from the collateral vessels 8, which would dilute the pharmacological fluid 50 reducing its effectiveness.

According to a possible operating mode, the drug supply step is performed in advance of the step of deflating at least partially the balloon. In other words, the start of the drug supply step is earlier than the start of the deflation step. For example, the start of the drug supply step is advanced by a predetermined time interval with respect to the start of the deflation step. According to a possible operating mode, the duration of the drug supply step is greater than the duration of the step of deflating at least partially the balloon. In this way, a temporary increase of pressure is generated in the at least one interstice 44, preventing the first fluid 30, for example physiological solution 30, which is placed between the pharmacological fluid 50 placed in the second portion 44 of the isolated volume 40 and the blood placed in the collateral vessels 8, from flowing back into the second portion 44 of the isolated volume 40 from one or more collateral vessels 8, thus allowing said vessel segment 5 to be treated to remain free of blood.

According to a possible operating mode, the method comprises the further step of repositioning the catheter shaft 20 in a further vessel segment 5 to be treated. This step is preferably performed by:

suction of the pharmacological fluid 50 from the interstitial volume 44 of the isolated volume 40;

volume contraction of the occlusion elements 42, 43 so as to disengage them from the wall of the vessel 4, longitudinal movement of the catheter shaft 20 until reaching said further vessel segment 5 to be treated, repetition of the treatment.

According to an embodiment, said catheter handle 10 and said catheter shaft 20 comprise a further path, in fluid communication with said interstitial volume 44, said further path is associated with a pressure sensor 76, 24, placed in the catheter handle 10 and/or in the catheter shaft 20, so as to monitor the pressure in the second portion 44 of the isolated volume 40 during the supply of fluid 30 or 50 in the second portion 44 of the isolated volume 40. Preferably, said further path is filled with first fluid 30.

According to a possible operating mode, a certain volume of drug is supplied first, preferably less than 2.0 milliliter or "ml", and preferably between 0.1 ml and 2.0 ml, and even more preferably between 0.1 and 1.0 ml.

According to a possible operating mode, the method comprises the further step of re-inflating the core balloon 41.

According to a possible operating mode, the method comprises the further step of taking the pharmacological fluid 50 from the interstitial volume 44.

Preferably, said step of inflating and said step of taking the pharmacological fluid are both performed simultaneously by means of a single control action by means of said synchronization device 60. In this way, the volume of said vessel segment 5 to be treated is kept substantially constant. This avoids leaving the pharmacological agent free in the bloodstream with potential side effects due to systemic toxicity.

According to a possible operating mode, the method comprises the further step of taking said first fluid 30 from said balloon 41. In this way, it is possible to empty or deflate said balloon 41, contracting it at least radially, and preferably both radially and longitudinally.

Preferably, this step of taking said first fluid 30 is performed by taking first fluid 30 from all the balloons 41, 42, 43 simultaneously, including also the occlusion elements 42, 43 when made in the form of expandable balloons. According to a possible operating mode, the method comprises the further step of taking said pharmacological fluid 50. In this way, it is possible to empty or deflate the second portion 44 of the isolated volume 40 from the residues of pharmacological agent when the administration of said pharmacological fluid 50 ends. Preferably, this step of taking said first fluid 30 is performed simultaneously with the step of taking said pharmacological fluid 50.

Due to the above features provided separately or jointly together in particular embodiments, it is possible to obtain a catheter which at the same time meets the above described requirements, which are in contrast with each other, and the above desired advantages, and in particular:

a variety of functions of the catheter handle 10 and therefore of the catheter 1 are made independent of the operator's ability;

a catheter handle with improved ergonomics compared to known solutions is provided;

the risk of human errors in the handling of the catheter and in the pharmacological treatment is reduced;

improved control of the drug treatment is provided;

a controlled dosage of drug is allowed in the area which laps the wall of the vessel in the isolated volume;

the amount of drug needed is reduced for the same effectiveness of therapy;

the catheter can be repositioned so as to repeat the treatment in vessel portions having different caliber;

it is possible to create an adjustment clearance of the first and second portions of the isolated volume by acting on a catheter handle which allows continuous volume adjustments;

it is possible to carry out a targeted drug therapy, for example a sclerosing treatment of varicose veins;

it is possible to use the vascular catheter in the localized treatment of other pathologies, for example as a device to access organs and systems.

Those skilled in the art may make several adjustments and replacements of elements with others which are functionally equivalent to the embodiments described above in order to meet incidental and specific needs, without departing from the scope of the following claims.

REFERENCE LIST

1 Vascular catheter
2 Blood vessel
3 Lumen
4 Vessel wall
5 Vessel segment to be treated, or vessel section to be treated
6 layer of the vessel wall
7 Muscle layer of the vessel wall
8 Collateral vessel
9 Induced lesion or micro-lesion
10 Catheter handle
11, 12, 13 Catheter paths
14 Proximal end of the catheter shaft
15 Handle casing
16 Handle window
17 Handle grip
18 Catheter shaft curve
19 Angle
20 Catheter shaft
24 First hole, or first shaft opening
25 Third hole, or third shaft opening
26 Second hole, or second shaft opening
27 Catheter sensor
30 First fluid, or inflation fluid, or physiological solution
31 First pumping device
32 First tank
33 First plunger
34 First rack
35 First tank conduit
38 Memory
39 Power supply
40 Isolated volume, or predefined intra-luminal volume
41 Expandable balloon, or core balloon
42, 43 Occlusion element, or expandable occlusion balloon
44 Second portion of isolated volume, or interstice, or interstitial volume
45 Balloon wall
50 Second fluid, or pharmacological fluid
51 Second pumping device
52 Second tank
53 Second plunger
54 Second rack
55 Second tank conduit
60 Synchronization device
61 Control interface
62 Drive interface of the synchronization device
63 Movable support
64 Gear unit
65 Electric motor
66 Elastic device
67 Stop
68 Leverage
69 Rocker arm
70 Connecting rod
71 Rack 72 Cam
73 Cam follower
74 Screw-nut assembly
75 Control device
76 Handle sensor
77 Signal device, for example a display
78 Adventitial tunica of the vessel wall
79 Control signal
80 Selector device
81 First valve
82 Second valve
83 Selector drive interface
84 Cap
85 Distal cap opening
86 Cap engagement portion
87 engagement counter-portion
88 Proximal cap opening
89 Cap compartment
90 First portion of the isolated volume
P1 First path
P2 Second path
R1 Rotation direction
X1 Longitudinal development direction of the handle
X2 Longitudinal development direction of the shaft
The invention claimed is:

1. A vascular catheter (1) comprising: —a catheter shaft (20) having a distal end, a proximal end (14), and a longitudinal axis (X2) therebetween, the catheter shaft (20) adapted to reach at least a predefined position in a blood vessel (2) in a patient; —a catheter handle (10) at the proximal end of the catheter shaft (20); —at least two occlusion elements (42, 43) fitted onto the catheter shaft (20) adapted to act as an occluder to isolate an isolated volume (40) of the blood vessel (2), the isolated volume (40) longitudinally interposed between said at least two occlusion elements (42, 43); —an expandable balloon (41), longitudinally interposed between the two occlusion elements (42, 43) and adapted to act as a core to occupy a first portion of the isolated volume (40) of the blood vessel (2) and thereby define a second portion (44) of the isolated volume (40) radially externally contouring a wall (45) of the expandable balloon (41); and at least two delivery and return catheter paths (11, 12, 13), independent from each other, which define in the vascular catheter (1) at least a first path (P1) and at least a second path (P2), distinct from the first path (P1); wherein the catheter shaft (20) comprises a first hole (24) which opens into the at least one expandable balloon (41); wherein the first hole (24) is in fluid communication with said first path (P1); wherein the catheter handle (10) comprises a first pumping device (31) associated with the first path and associable with a first tank (32) containing a first fluid (30); wherein the catheter shaft (20) comprises a second hole (26) which opens out of the at least one expandable balloon (41) so as to be adapted to lead into said second portion (44) of said isolated volume (40); wherein the second hole (26) is in fluid communication with said second path (P2); wherein the catheter handle (10) comprises a second pumping device (51) associated with the second path and associable with a second tank (52) containing a second, pharmacological fluid (50) which contains drug; wherein the catheter handle (20) comprises a synchronization device (60) operatively connectable both to the first pumping device (31) and to the second pumping device (51) and at least one drive interface for controlling said synchronization device (60); wherein both said first tank (32) and said second tank (52) act as a collection tank and a storage tank for the respective fluid, said first and second paths (P1, P2) allowing the respective fluid to travel in both directions, so that the catheter shaft (10) can be repositioned in various portions of the blood vessel (2) having different caliber to create said isolated volume (40); wherein said first pumping device (31) comprises at least a first plunger (33), adapted to slide within the first tank (32), the first tank comprising at least one cylinder in fluid connection with at least one handle path (11, 12, 13), so as to form a first syringe; wherein said second pumping device (51) comprises at least a second plunger (53), adapted to slide within the second tank (52), the second tank comprising at least one cylinder in fluid connection with at least one handle path (11, 12, 13), so as to form a second syringe; wherein said synchronization device (60) is configured to: decouple, at least for a predefined free stroke, in response to a first manual operation of the at least one drive interface, the stroke of said first plunger (33) within said first tank (32) from the stroke of said second plunger (53) within said second tank (52) while said second pumping device (51) supplies the second, pharmacological fluid (50) to the second portion (44) of the isolated volume (40) as a result of movement of said second plunger (53) in a first direction, and without reduction in volume of the expandable balloon (41) to create an overpressure in the second portion (44) of the isolated volume (40), and couple, in response to a second manual operation of the at least one drive interface, the stroke of said first plunger (33) within said first tank (32) to the stroke of said second plunger (53) within said second tank (52) to deliver in said isolated volume (40) a predetermined volume of the second, pharmacological fluid (50) out of the at least one expandable balloon (41) as a result of movement of said second plunger (53) in the first direction, simultaneously causing a reduction in volume of the expandable balloon (41) by an equal predetermined volume as a result of coupled movement of said first plunger (31) in a second direction opposite to the first direction.

2. The vascular catheter (1) according to claim 1, wherein said synchronization device (60), when operatively connected to both said first pumping device (31) and said second pumping device (51), is further configured to take from said isolated volume (40) a predetermined volume of second, pharmacological fluid (50), simultaneously causing an expansion of volume of the expandable balloon (41) by an equal predetermined volume.

3. The vascular catheter (1) according to claim 1, wherein said at least two occlusion elements (42, 43) consist of two expandable occlusion balloons.

4. The vascular catheter (1) according to claim 3, wherein the expandable balloon (41) adapted to act as a core is in one piece with an expandable occlusion balloon (42 or 43).

5. The vascular catheter (1) according to claim 1, wherein the synchronization device (60) is operatively connected to both said first pumping device (31) and said second pumping device (51), said catheter handle (10) supplies a predetermined volume of second, pharmacological fluid (50) and takes an equal predetermined volume of first fluid (30) by a single control action by an operator of the catheter handle (10) on a control interface (61).

6. The vascular catheter (1) according to claim 3, wherein: —the catheter handle (10) further comprises a selector device (80) in fluid connection both with said first tank (32) and with said at least two delivery and return paths (11, 12, 13), —said at least two delivery and return paths (11, 12, 13) are at least three delivery and return paths comprising: a core balloon path (11) fluidly connected with said at least a first hole (24) which opens into said at least one expandable core balloon (41), and an occlusion balloon path (12) fluidly connected with at least a third hole (25) which opens into said at least two occlusion elements (42, 43); —said selector device (80) is configured to temporarily occlude at least one delivery and return path (11 or 12 or 13) of said at least two delivery and return paths (11, 12, 13) at a time; and—said selector device (80) comprises at least a first valve (81), adapted to occlude at least one of: said core balloon path (11) and said occlusion balloon path (12).

7. A method of handling a catheter comprising the following steps of: —providing a vascular catheter (1) according to—providing a vascular catheter (1) according to—disposing at least a portion of said vascular catheter (1) inside a lumen of a blood vessel (2) that includes a blood vessel segment (5) to be treated, wherein the method comprises the following treatment steps: a—dispensing said first fluid (30) inside said expandable balloon (41) by means of said first pumping device (31), inflating said expandable balloon (41) to be expanded at least radially, b—bringing said expandable balloon (41) into contact with a vessel wall (4) of the blood vessel (2), c—expanding said at least two occlusion elements (42, 43) at least radially, to form an occlusion which, adhering to vessel walls (4) along at least a cross section of said blood vessel (2), isolates an isolated volume (40) of the blood vessel (2) to be treated from the circulatory system, the isolated volume (40) longitudinally interposed between said at least two occlusion elements, d—supplying said second, pharmacological fluid (50) by means of said second pumping device (51) in a second portion (44) of the isolated volume (40) to create an over-pressure in the second portion (44), the second portion (44) of the isolated volume (40) being located between the wall (45) of said expandable balloon (41) and the vessel wall (4) of the blood vessel segment (5) to be treated, and, subsequently, further supplying said second, pharmacological fluid (50) into the over-pressurized second portion (44), e—deflating at least partially said expandable balloon (41) by withdrawing said first fluid (30) from the expandable balloon (41), and f—synchronizing the volume of said second, pharmacological fluid (50) supplied in the second portion (44) of the isolated volume (40) with the volume of the first fluid (30) withdrawn from the expandable balloon (41), wherein the step d—is carried out at the same time as the step e—, to keep the isolated volume (40) of said blood vessel segment (5) to be treated constant, and wherein the step f—is performed after activating, or operating, said synchronization device (60) operatively connected to both said first pumping device (31) and said second pumping device (51).

8. The method of handling a catheter according to claim 7, further comprising the following treatment step: g—continuing to dispense said first fluid (30) inside said expandable balloon (41) by means of said pumping device (31), causing an over-inflation of said expandable balloon (41), so to create on the vessel wall (4) a series of lesions (9) of a layer of vessel wall facing the lumen (3) of said blood vessel (2).

9. The method of handling a catheter according to claim 8, wherein the step g—is carried out after the step b—, so that during the step g—, the wall (45) of the expandable balloon (41) is in contact with the wall (4) of the blood vessel (2) and the wall of the expandable balloon transmits an action aimed at over-extending the wall (4) of the blood vessel (2); and/or wherein the step g—is carried out before the step d—so as to allow the second pharmacological fluid (50) to soak at least one deep layer of the vessel wall (4).

10. The method of handling a catheter according to claim 8, further comprising the following treatment steps:

h—monitoring a stress state and/or deformation state, of said expandable balloon (41); wherein the step h—is carried out by means of at least one catheter sensor (27) or by at least one handle sensor (76), wherein said at least one handle sensor (76) comprises at least one pressure sensor (76).

11. The method of handling a catheter according to claim 10, wherein said handle sensor (76) is operatively connected to at least one memory (38), which is configured to store information on the stress state and/or the deformation state of said expandable balloon detected by said at least one handle sensor (76) at predefined instants of time during the steps of the method, wherein said memory (38) is associated with a control device (75), wherein the control device (75) records the variation over time of the pressure increase rate, and consequently of volume, inside said expandable balloon (41) to facilitate monitoring the over-inflation of the expandable balloon (41), while allowing control of the over-inflation of the expandable ballon and, therefore, to obtain a qualitative control on the extent of the lesions (9) induced on the inner layer (6) of the wall (4) of the blood vessel (2), and/or wherein the step h—can be performed at any time in the method; and/or the step h—is performed simultaneously at least with the steps of bringing the wall (45) of the expandable balloon (41) into contact with the wall (4) of the blood vessel (2) and of continuing the supply.

12. The method of handling a catheter according to claim 11, wherein the control device (75) activates an indicator to signal to an operator the stress state and/or the deformation state of the expandable balloon; and/or wherein said control device (75) activates said indicator, comprising a sound indicator, adapted to emit an acoustic signal to signal that the expected over-inflation has occurred; and/or wherein said control device (75) automatically transmits control signals (79) to the first pumping device (31) on the basis of the information stored in said memory (38) and processed by said control device (75).

13. The method of handling a catheter according to claim 7, further comprising the following treatment step: i—dispensing the first fluid (30) into the second portion (44) of the isolated volume (40), so as to remove a minimum residual blood content contained in the second portion (44) of the isolated volume (40) towards at least a collateral branch (8), which branch off from the wall (4) of the vessel segment (5) to be treated.

14. The method of handling a catheter according to claim 7, further comprising the following treatment step: l—monitoring the supply of the second, pharmacological fluid (50) and/or the deflation of said expandable balloon (41), wherein the step l—is performed by at least one flow meter (76) and or at least one pair of flow meters (27, 76), of which at least one flow meter is placed in fluid communication with the second portion (44) of the isolated volume (40) and at least one flow meter is placed in fluid communication with said expandable balloon (41), allows monitoring a flow rate of the second, pharmacological fluid (50) supplied in the second portion (44) of the isolated volume (40) and a flow rate of the first fluid (30) withdrawn from said expandable balloon (41).

15. The method of handling a catheter according to claim 14, wherein a control device (75) processes the information on the flow rates acquired by said at least one flow meter (76, 27) to process it and transmit control signals to said synchronization device (60), and/or wherein the step d—is performed simultaneously with the step e—automatically, on the basis of information detected by a detection device and processed by a control device (75) which transmits control signals (79) to said synchronization device (60), and/or wherein the monitoring the supply of the drug and/or the deflation step comprises the step of detecting the flow rate of the first fluid (30) leaving the expandable balloon (41) which forms the first portion (90) of the isolated volume (40), and/or wherein the monitoring step comprises the step of detecting the flow rate of pharmacological fluid (50) entering the second portion (44) of the isolated volume (40), and/or wherein the step l—is performed by comparing the flow rate of the first fluid (30) leaving the expandable balloon (41) with the flow rate of pharmacological fluid (50) entering the second portion (44) of the isolated volume (40).

16. The method of handling a catheter according to claim 7, comprising a step m—of repositioning the catheter shaft (20) in a further vessel segment (5) to be treated, wherein the step m—is performed by: —suction of the second pharmacological fluid (50) from the second portion (44) of the isolated volume (40); —volume contraction of the at least two occlusion elements (42, 43) so as to disengage them from the wall of the vessel (4), —longitudinal movement of the catheter shaft (20) until reaching said further vessel segment (5) to be treated, —repetition of said treatment steps; wherein the repetition of said treatment steps is performed by adapting the catheter to portions of blood vessels of various dimensions so that to adapt the volume of said second, pharmacological fluid (50) and the dimensions of the at least two occlusion elements (42, 43) to the dimensions of said further vessel segment (5) to be treated by means of said synchronization device (60).

17. The method of handling a catheter according to claim 7, wherein the step d—is carried out by pressing a plunger (53) of a syringe, and/or wherein the step d—is performed by pressing a supply actuation control and/or wherein the step e—is carried out by pulling a plunger (33) of a syringe, and/or wherein the step e—is performed by pressing a deflation actuation control and/or wherein the step d—determines, when said synchronization device (60) is in operating conditions, the simultaneous activation of the step e—, and/or wherein pressing said second plunger (53) causes the simultaneous movement in opposite direction of said first plunger (33), and/or wherein by operating said second pumping device (51) the simultaneous actuation in opposite direction of said first pumping device (31) is determined.

* * * * *